(12) United States Patent
Winterberg et al.

(10) Patent No.: US 8,841,492 B2
(45) Date of Patent: Sep. 23, 2014

(54) METHOD FOR PURIFICATION OF MIXTURES COMPRISING MTBE AS WELL AS PRODUCTION OF ISOBUTENE BY SPLITTING OF MIXTURES COMPRISING MTBE

(75) Inventors: Markus Winterberg, Datteln (DE); Dirk Roettger, Cologne (DE); Armin Rix, Marl (DE); Reiner Bukohl, Marl (DE); Christian Boeing, Cologne (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/880,862

(22) PCT Filed: Oct. 12, 2011

(86) PCT No.: PCT/EP2011/067770
§ 371 (c)(1),
(2), (4) Date: Jul. 3, 2013

(87) PCT Pub. No.: WO2012/052327
PCT Pub. Date: Apr. 26, 2012

(65) Prior Publication Data
US 2013/0303806 A1      Nov. 14, 2013

(30) Foreign Application Priority Data

Oct. 21, 2010   (DE) .................. 10 2010 042 774

(51) Int. Cl.
C07C 41/42    (2006.01)
C07C 1/20     (2006.01)
C07C 7/10     (2006.01)

(52) U.S. Cl.
CPC . *C07C 41/42* (2013.01); *C07C 1/20* (2013.01); *C07C 7/10* (2013.01)
USPC ........................................ 568/699

(58) Field of Classification Search
USPC ....................................... 568/699
See application file for complete search history.

(56) References Cited

U.S. PATENT DOCUMENTS

| | | | | |
|---|---|---|---|---|
| 4,144,138 A * | 3/1979 | Rao et al. | ......... | 203/46 |
| 4,334,964 A * | 6/1982 | Prezelj et al. | .......... | 203/14 |
| 4,943,354 A * | 7/1990 | Osterburg et al. | .............. | 203/14 |
| 5,157,163 A * | 10/1992 | Smith et al. | ................... | 568/699 |
| 5,159,122 A | 10/1992 | Sanderson et al. | | |
| 6,657,090 B2 | 12/2003 | Rix et al. | | |
| 7,304,188 B2 * | 12/2007 | Obenaus et al. | .............. | 568/699 |
| 7,361,714 B2 | 4/2008 | Grass et al. | | |
| 7,473,812 B2 | 1/2009 | Peters et al. | | |
| 7,737,318 B2 | 6/2010 | Santiago-Fernandez et al. | | |
| 7,910,786 B2 | 3/2011 | Winterberg et al. | | |
| 7,919,662 B2 | 4/2011 | Winterberg et al. | | |
| 7,932,428 B2 | 4/2011 | Rix et al. | | |
| 7,968,758 B2 | 6/2011 | Winterberg et al. | | |
| 7,977,523 B2 | 7/2011 | Zanthoff et al. | | |
| 8,269,050 B2 | 9/2012 | Praefke et al. | | |
| 2006/0041167 A1 | 2/2006 | Grass et al. | | |
| 2008/0058572 A1 | 3/2008 | Fernandez et al. | | |
| 2010/0144998 A1 | 6/2010 | Santiago-Fernandez et al. | | |
| 2011/0118523 A1 | 5/2011 | Winterberg et al. | | |
| 2011/0152596 A1 | 6/2011 | Zanthoff et al. | | |
| 2011/0217552 A1 | 9/2011 | Schulze-Isfort et al. | | |
| 2012/0142985 A1 | 6/2012 | Winterberg et al. | | |
| 2012/0149549 A1 | 6/2012 | Boeing et al. | | |

FOREIGN PATENT DOCUMENTS

DE    10 2008 040511    1/2010
WO    2012 123292      9/2012

OTHER PUBLICATIONS

International Search Report Issued Apr. 20, 2012 in PCT/EP11/067770 Filed Oct. 12, 2011.
U.S. Appl. No. 13/997,677, filed Jun. 25, 2013, Schulze-Isfort, et al.
U.S. Appl. No. 14/005,479, filed Sep. 16, 2013, Winterberg, et al.

* cited by examiner

*Primary Examiner* — Brian J Davis
(74) *Attorney, Agent, or Firm* — Oblon, Spivak, McClelland, Maier & Neustadt, L.L.P.

(57) ABSTRACT

The present invention relates to a process for efficient purification of MTBE-containing mixtures and for preparation of isobutene by cracking of MTBE-containing mixtures.

20 Claims, 4 Drawing Sheets

METHOD FOR PURIFICATION OF MIXTURES COMPRISING MTBE AS WELL AS PRODUCTION OF ISOBUTENE BY SPLITTING OF MIXTURES COMPRISING MTBE

The present invention relates to a process for efficient purification of MTBE-containing mixtures and for preparation of isobutene by cracking of MTBE-containing mixtures.

"High boilers" in the context of the invention are a group of components of a liquid substance mixture whose respective boiling points are at higher temperatures compared to the boiling points of the other components of the substance mixture, or whose vapour pressures are lower than the vapour pressures of the other components. The term "high-boiling components" is used synonymously to the term "high boilers".

"Low boilers" in the context of the invention are a group of components of a liquid substance mixture whose respective boiling points are at lower temperatures compared to the boiling points of the other components of the substance mixture, or whose vapour pressures are higher than the vapour pressures of the other components. The term "lower-boiling component" is used synonymously to the term "low boilers".

Isobutene is an important intermediate for the preparation of a multitude of organic compounds, for example for the preparation of butyl rubber, polyisobutylene, isobutene oligomers, branched $C_5$ aldehydes, $C_5$ carboxylic acids, $C_5$ alcohols and $C_5$ olefins. In addition, it is used as an alkylating agent, especially for synthesis of tert-butylaromatics, and as an intermediate for obtaining peroxides. In addition, isobutene can be used as a precursor for methacrylic acid and esters thereof.

Isobutene is present in customary technical streams together with saturated and unsaturated $C_4$ hydrocarbons. Owing to the small boiling point difference and the low separation factor between isobutene and 1-butene, isobutene cannot be removed economically from these mixtures by distillation. Isobutene is therefore frequently obtained from technical hydrocarbons by converting isobutene to a derivative which can be removed easily from the remaining hydrocarbon mixture, and by back-cracking the isolated derivative to isobutene and derivatizing agent.

Typically, isobutene is removed from $C_4$ cuts, for example the $C_4$ fraction of a steamcracker, as follows: after removing the majority of the polyunsaturated hydrocarbons, principally the butadiene, by extraction and distillation or selective hydrogenation to linear butenes, the remaining mixture (raffinate I or selectively hydrogenated crack $C_4$) is reacted with alcohol or water. Isobutene forms methyl tert-butyl ether (MTBE) when methanol is used, and tert-butanol (TBA) when water is used. After they have been removed, these derivatives can be cracked to isobutene in a reversal of their formation.

Technical MTBE is a sought-after component in fuels for gasoline engines to increase the octane number. In this case, the requirements with regard to purity are not very high. The methanol and tert-butanol contents may each be up to 1% by mass. In addition, technical MTBE may comprise up to 0.5% by mass of C4- to C8-hydrocarbons and up to 500 ppm of water. In higher purities, MTBE is also used as a solvent and extractant in the pharmaceutical sector and in analysis.

The cracking of MTBE to isobutene and methanol can be carried out in the presence of acidic or basic catalysts in the liquid phase or gas/liquid mixed phase or in the pure gas phase. One good review of the known processes can be found in R. Trotta and I. Miracca in Catalysis Today 34 (1997), p. 447 to 455.

U.S. Pat. No. 5,567,860 describes a process for preparing high-purity isobutene. Here, isobutene-containing $C_4$ streams are first etherified with methanol, such that, according to the conversion, a mixture of MTBE, 2-methoxybutane (MSBE), unconverted $C_4$ hydrocarbons, methanol, water, dimethyl ether (DME), $C_4$ oligomers, and $C_3$ and $C_5$ hydrocarbons as an impurity of the $C_4$ stream, is obtained. This product mixture is separated by distillation into low boilers containing $C_3$, $C_4$ and $C_5$ hydrocarbons, methanol and DME, and high boilers containing $C_4$ oligomers. In a side draw of the column, MTBE and 2-methoxybutane (MSBE) are obtained, which are then fed to the acid-catalysed cracking.

DE 10 2006 040431 describes a process for preparing isobutene by MTBE cracking. In this process, starting MTBE together with a recycled MTBE stream are purified in a column by removing high boilers, and the resulting MTBE is cracked. The reaction effluent is separated by distillation into isobutene with (azeotropic) proportions of methanol, and a mixture comprising the main constituents of methanol and unconverted MTBE. The methanol is subsequently removed for the most part from the methanol/MTBE mixture, and the MTBE-containing stream is recycled into the column for removal of high boilers. Optionally, low boilers are removed from the starting MTBE.

Specification DE 10 2006 040430 is based on a comparable process. Characteristic features are purification of the MTBE used in the cracking to less than 1000 ppm by mass of 2-methoxybutane, and concentrations of linear butenes in the isobutene obtained below 1000 ppm by mass. The recycling of unconverted MTBE is optional.

In DE 10 2008 040511, medium-boiling components are discharged by conducting the output from the MTBE cracking, after removal of isobutene and the majority of the methanol, into a distillation to remove these medium-boiling components and then recycling it into the cracking. The medium boilers can optionally be discharged together with the low boilers present in the starting MTBE in the lower boiler removal.

DE 10 2009 027404 describes a combination of MTBE synthesis and MTBE cracking, wherein unconverted MTBE and methanol are conducted from the MTBE cracking back into the MTBE synthesis. Water is removed from this return stream in order to prevent a reduction in activation of the synthesis catalyst.

DE 10231051 describes a process for preparing high-purity MTBE by double distillation. The process is notable for a very high purity of the MTBE obtained (>99.7% by mass) and for relatively large by-product streams which, in addition to the secondary components removed from the MTBE, such as C4 and C5 hydrocarbons, TBA, methanol and 2-methoxybutane, also comprise MTBE to a significant degree. The MTBE obtained is suitable as a reactant for MTBE cracking for preparation of high-purity isobutene.

The formation of high boilers by dimerization or oligomerization of the isobutene to $C_4$ oligomers, known as $C_8$ and $C_{12}$ components, is one of the known side reactions in MTBE cracking. The undesired $C_8$ components are principally 2,4,4-trimethyl-1-pentene and 2,4,4-trimethyl-2-pentene. In addition, particularly over basic catalysts, a portion of the methanol formed in the cracking is converted to DME with elimination of water.

The further workup of the methanol-containing isobutene streams obtained in DE 10 2006 040431 and DE 10 2006 040430 therefore envisages a removal of the methanol by extraction with water and a subsequent distillation, in which DME and water are removed from the isobutene.

MTBE cracking in the gas phase has the advantage that it generally proceeds at higher temperatures. The equilibrium of the reaction of MTBE to give isobutene and methanol is thus more to the side of the products, such that higher conversions can be achieved. Owing to the higher cracking temperatures, however, other and/or additional side reactions can occur.

As described at the outset, isobutene is an important intermediate for the preparation of a multitude of organic compounds. The efficient preparation of these products is a core area of current industrial research and therefore places very high demands on the product purity. Table 1 shows a typical specification for isobutene available on the market. A particularly notable feature, in addition to the high isobutene purity required (>99.9% by mass), is the severe specification for oxygenates (max. 10 ppm by mass). For special applications, an even higher purity may even be required in the individual case.

TABLE 1

Typical composition of isobutene available on the market
Parts by mass [kg/kg]

| | |
|---|---|
| C3 hydrocarbons | <0.000100 |
| butanes | <0.001000 |
| isobutene | >0.999000 |
| 1-butene/2-butenes | <0.001000 |
| methanol | <0.000030 |
| C5 hydrocarbons | <0.000500 |
| water | <0.000050 |
| oxygenates | <0.000010 |

Oxygenates: for example DME, acetone

C4 cuts which are used for the MTBE synthesis, however, generally comprise not only the C4 hydrocarbons but also oxygen compounds. The type and amount of the oxygen compounds depend on the type and origin of the raw material streams used and the technical conditions selected in the crackers. The further workup of the C4 cut also influences the content of these impurities. The oxygen compounds are, for example, acetaldehyde and acetone. As a result of the preparation, at least some of the acetone in the MTBE synthesis gets into the MTBE product. Thus, MTBE available on the market comprises not only 2-methoxybutane, C3 to C4 hydrocarbons, methanol, water and DME but also acetone. When the MTBE product is used for preparation of isobutene and acetone is not removed before the MTBE cracking, it gets into the reaction section. Under some circumstances, it can contribute here to deactivation of the catalyst, for example by coking. If acetone is not converted, it can accumulate in the process and ultimately gets into the isobutene product, which is likewise undesirable since oxygen compounds can disrupt the downstream processes in which the high-purity isobutene goes on to be used. Possible downstream processes are, for example, the preparation of polyisobutene (PIB), butyl rubber or else methyl methacrylate (MMA).

None of the MTBE purification and MTBE cracking processes mentioned and described in the literature provides for the explicit removal of acetone. Most of the processes provide for partial conversion in the MTBE cracking, unconverted MTBE and methanol being removed from the isobutene in a distillation arranged downstream of the reaction and being conducted either back into an MTBE synthesis or back into the MTBE cracking. In the case of removal of acetone via the bottom product of this distillation, however, the recycling of the unconverted MTBE either into the MTBE synthesis or into the MTBE cracking results in enrichment of the acetone in the process. If acetone passes through the reactor without further reaction, the concentration thereof rises up to a limiting concentration at which it finally gets into the top product of the distillation arranged downstream of the reactor and thus ultimately into the isobutene fraction after all. The circulation method thus results, without discharge of acetone from the process in the circulation, in an enrichment to undesirably high concentrations until acetone finally gets into the isobutene fraction. The workup steps typically arranged downstream of distillation—an extraction with water to remove methanol and a distillation to remove dimethyl ether from isobutene—do not lead to removal of acetone from the isobutene product. Thus, in the absence of discharge of acetone from the process, the product would be contaminated and no longer meet the customary oxygenate specification; see table 1. The total specification of <10 ppm by mass required therein is very demanding particularly because not only acetone but also further oxygen compounds, e.g. dimethyl ether (DME), are present in the isobutene product as a result of preparation and likewise have to be removed. Purification of the isobutene is also conceivable, for example by distillation or by adsorption, as proposed, for example, in EP 1562883 and US2004 0102656. However, this purification constitutes an additional workup step and would disproportionately reduce the effectiveness of the process as a result of the associated higher apparatus complexity and the high energy expenditure for distillation or for the regeneration of the adsorbent.

In the processes known from the literature, for example DE 10 2009 027404, the MTBE-containing feedstock (I) is at least optionally free of low boilers by distillation. The low boilers are predominantly C4 or C5 hydrocarbons. The distillation column is operated in such a way that the low boilers are removed as the top product and the bottom product comprises the low boilers (C4 hydrocarbons, C5 hydrocarbons and any oxygen compounds such as dimethoxymethane) only up to those limiting concentrations which do not endanger the appropriate specification in the isobutene product (see table 1).

TABLE 2

Pure substance boiling points of components which typically occur in the cracking process at 0.1 and 0.5 MPa$_{(abs)}$

| Pure substance | Boiling temp.[° C.] at 0.1 MPa(abs) | Boiling temp.[° C.] at 0.5 MPa(abs) |
|---|---|---|
| DME | −24.8 | 19.2 |
| isobutene | −6.9 | 42.7 |
| 1-butene | −6.3 | 43.4 |
| n-butane | −0.5 | 50.3 |
| trans-2-butene | 0.9 | 51.4 |
| cis-2-butene | 3.7 | 54.1 |
| isopentane | 27.8 | 83.8 |
| 1-pentene | 30.0 | 85.5 |
| isoprene | 34.1 | 90.4 |
| n-pentane | 36.1 | 92.6 |
| dimethoxymethane | 41.9 | 95.9 |
| methanol | 64.7 | 111.5 |
| acetone | 56.3 | 111.7 |
| MTBE | 55.2 | 113.8 |
| 2-methoxybutane | 59.0 | 120.8 |
| TBA | 82.4 | 131.3 |
| diisobutene | 101.4 | 171.2 |

Table 2 lists the standard boiling points for various components which are typically either present in the MTBE-containing feedstock or else are formed in the reaction section in the process according to the invention. Since many distillations in the process according to the invention are preferably performed under elevated pressure, the boiling points at 0.5 $MPa_{(abs)}$ are additionally listed in the table. As can be seen, acetone boils very close to MTBE; at elevated pressure, acetone boils between MTBE and methanol. Furthermore, acetone forms azeotropes both with methanol and with MTBE. Therefore, acetone in customary operation of the distillation for low boiler removal does not get into the distillate and is therefore not removed.

In principle, simultaneous removal of acetone in this distillation is conceivable. Typically, the low boiler removal is conducted in such a way that the bottom product is very substantially free of C4 and C5 hydrocarbons and that the top product comprises a minimum amount of MTBE and methanol, since the top product is discharged from the process (MTBE concentration<25% by mass). Acetone can then be discharged only into the top product, by operating the distillation with a much higher amount of distillate (MTBE concentration>65% by mass) and possibly also with simultaneous increased reflux. Therefore, such a removal by simple distillation of the acetone together with other lower-boiling components is associated with a disproportionately high energy expenditure and high MTBE and methanol losses. The distillate stream, due to the high proportion of C4 and C5 hydrocarbons, is also unsuitable as a fuel additive without another workup.

It was therefore an object of the present invention to provide a process for preparing high-purity MTBE from technical MTBE, in which the technical MTBE is freed of acetone in an effective and economically viable manner and hence the process affords an MTBE which is suitable, inter alia, for preparation of high-purity isobutene.

The object was achieved by subjecting the MTBE-containing feedstock to a distillation in which the acetone is removed predominantly in a side stream. As well as acetone, the side stream comprises predominantly MTBE and methanol. The top stream of the distillation comprises predominantly C4 and C5 hydrocarbons, and the bottom stream comprises predominantly MTBE.

The invention therefore provides a process for purifying technical MTBE, which comprises the following steps:
  a) providing technical MTBE (I) comprising at least MTBE, methanol, C4 hydrocarbons, C5 hydrocarbons and acetone; and
  b) distillatively separating the technical MTBE (I) into a top product (II) comprising C4 and C5 hydrocarbons, a side stream (III) comprising acetone, methanol and MTBE, and a bottom product (IV) comprising MTBE.

Compared to the closest prior art, described in DE 10 2006 040431, DE 10 2006 040430 and DE 10238370, the process according to the invention has the advantage that acetone is discharged in a controlled and effective manner.

Preferably, the distillative separation in process step b) is performed in such a way that the bottom product (IV) comprises less than 50% by mass of the acetone present in the technical MTBE (I).

The distillative separation in process step b) is typically performed in a distillation column and the side stream (III) is withdrawn in liquid form.

It is optionally also possible to remove high boilers, in particular C8 hydrocarbons, from the bottom product (IV) obtained in step b) in a process step c). Therefore, in a preferred embodiment, after process step b), the bottom product (IV) of the first distillation is purified further in a further distillation. In this distillation, higher-boiling components than MTBE, i.e. high boilers, in particular C8 hydrocarbons, can be removed as bottom product (V). A further task of this column may be the partial or complete removal of 2-methoxybutane; this is because 2-methoxybutane can be cracked in the reaction section to give linear butenes and methanol; linear butenes at excessively high concentration can in some cases endanger the isobutene specification. The MTBE-containing top product (VI) of the distillation can optionally, on account of its purity, be used as a solvent and extractant in the pharmaceutical sector.

A preferred embodiment of the process according to the invention thus provides for separation of the bottom product (IV) from process step b) in a process step c) in a further distillation into an MTBE-containing top product (VI) and a bottom product (V) comprising higher-boiling components than MTBE.

The distillative separation in process step c) can preferably be performed in such a way that the MTBE-containing top product (VI) has a concentration of less than 2500 ppm by mass of 2-methoxybutane.

The distillative separations are preferably performed in such a way that the MTBE-comprising bottom product (IV) or the MTBE-containing top product (VI) comprises less than 50 ppm by mass of acetone.

Stream (IV) or, after high boiler removal, stream (VI) is particularly suitable as feedstock for preparation of high-purity isobutene by catalytic cracking.

A preferred embodiment of the process according to the invention thus provides for catalytic cracking of the MTBE-comprising bottom product (IV) or the MTBE-containing top product (VI) in a process step d) to obtain a cracking product (VII) comprising at least MTBE, isobutene and methanol. The cracking is preferably performed over a solid catalyst in the gas phase within a temperature range from 150 to 500° C.

The cracking product (VII) obtained in process step d) is separated in a process step e) in a further distillation into an isobutene-comprising top product (IX) and an MTBE- and methanol-comprising bottom product (VIII).

The invention thus also provides for the preparation of high-purity isobutene, characterized by the steps of:
  d) cracking the MTBE present in stream (IV) or in stream (V) over a heterogeneous catalyst to obtain a stream (VII) comprising at least MTBE, methanol and isobutene, and
  e) distillatively separating stream (VII) into a top product (IX) at least comprising isobutene, and a bottom product (VIII) at least comprising MTBE and methanol.

The isobutene-comprising top product (IX) which is obtained in process step e) comprises preferably less than 10 ppm by mass of acetone.

The MTBE present in stream (VIII) is preferably recycled into the reaction section of the MTBE cracking. For this purpose, in a further distillation, the methanol is preferably removed as the bottom product and an MTBE- and methanol-comprising stream is returned to the cracking. Particular preference is given to recycling into step b) of the process according to the invention. Alternatively, the recycling can also be effected into an MTBE synthesis, in which case no methanol removal is required but may be advantageous. Preference is given to recycling into the MTBE synthesis from which the MTBE-containing stream for process step a) also originates.

In a preferred embodiment of the process according to the invention, methanol can be removed by extraction and/or dimethyl ether by distillation in a further process step f) from the top product (IX) which is obtained in process step e) and comprises isobutene.

More preferably, the methanol is removed from the isobutene-comprising top product (IX) by extraction by means of an extractant (XIII) and removing a methanol-comprising extraction stream (XI) and removing an isobutene-enriched stream (X).

In a preferred embodiment of the process according to the invention, the methanol-comprising extraction stream (XI) can be separated in a further process step in a distillation into a methanol-comprising top product (XII) and a bottom product (XIII) comprising the extractant (XIII).

In addition, the bottom product (VIII) which is obtained in process step e) and comprises MTBE and methanol can be fully or partly, optionally also after further workup, recycled into process step b). The bottom product (VIII) can be provided in process step a) instead of the technical MTBE (I) or in addition to the technical MTBE (I), and then separated by distillation in process step b).

In a preferred embodiment of the process according to the invention, the MTBE- and methanol-comprising bottom stream (VIII) can be separated in a further process step in a distillation into a methanol-comprising bottom product (XVIII) and an MTBE-comprising top product (XVII), said top product (XVII) being recycled fully or partly into process step b).

In an alternative embodiment, in a further process step, the MTBE- and methanol-comprising bottom stream (VIII) and at least one further methanol-containing stream (XXI) and an isobutene-containing stream (XX) can be supplied to an MTBE synthesis and an MTBE-containing product (XXII) can be recycled fully or partly into process step b).

The isobutene (IX) obtained in process step e), which in accordance with the invention is virtually free of acetone and consists preferably to an extent of greater than 95% by mass of isobutene, can then be used directly as a saleable product or else, as mentioned, be purified further. Preferably, the isobutene (IX) is worked up further in a process step f). In this case, the methanol present in stream (IX) can be removed by known processes, for example by extraction. The extraction of methanol from stream (IX) can be performed, for example, with water or an aqueous solution as an extractant, for example in an extraction column.

The moist isobutene stream (X) from the extraction can be separated in a further distillation from dimethyl ether and water and worked up to give dry isobutene. The dry isobutene is obtained as the bottom product (XVI). In the condensation system at the top of the column, after phase separation, water (XIV) is drawn off in liquid form and dimethyl ether (XV) in gaseous form.

The invention is described by way of example hereinafter, without any intention that the invention, the scope of protection of which is evident from the claims and the description, be restricted thereto. The claims themselves also form part of the disclosure-content of the present invention. When ranges, general formulae or compound classes are specified hereinafter, the disclosure shall cover not only the appropriate ranges or groups of compounds mentioned explicitly but also all sub-ranges and sub-groups of compounds which can be obtained by omitting individual values (ranges) or compounds, without these having been mentioned explicitly for reasons of better clarity.

PROCESS STEP A

Provision of the MTBE-Containing Feedstock

Figure 1:
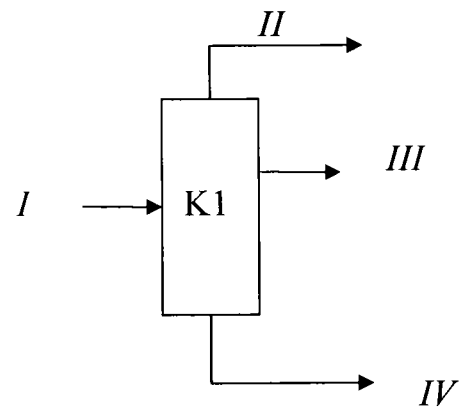
FIG. 1 is a block diagram of a first preferred embodiment of a process for purifying technical MTBE according the invention.

The present invention relates to a process for efficient purification of MTBE-containing mixtures and for preparation of isobutene by cracking of MTBE-containing mixtures. It is possible to use MTBE of different quality. More particularly, it is possible to use technical MTBE of different qualities or mixtures of technical MTBE and methanol. Technical MTBE (fuel quality) is therefore the preferred feedstock. Table 3 shows, by way of example, the typical composition of a technical MTBE.

TABLE 3

| Typical composition of technical MTBE (fuel quality) | | |
|---|---|---|
| Component | Content | Unit |
| C4 HC | 100-1200 | ppm by mass |
| C5 HC | 500-2000 | ppm by mass |
| MTBE | 97-99.0 | % by mass |
| 2-methoxybutane (MSBE) | 1000-3500 | ppm by mass |
| methanol | 0.3-1.0 | % by mass |
| tert-butanol | 1000-5000 | ppm by mass |
| water | 5-500 | ppm by mass |
| C8 HC | 1000-4000 | ppm by mass |
| acetone | 10-500 | ppm by mass |

Technical MTBE can be prepared by known processes by reaction of C4 hydrocarbon mixtures from which the polyunsaturated hydrocarbons have been substantially removed, for example raffinate I or selectively hydrogenated crack-C4, with methanol (MTBE synthesis). In principle, it is possible for this purpose to use all known processes for MTBE synthesis; for example, the MTBE synthesis can be effected analogously to the description in DE 101 02 082.

The MTBE synthesis is preferably performed in at least two, more preferably in three, fixed bed reactors. The reactors used, in which the methanol is reacted with the isobutene as far as close to the thermodynamic equilibrium, may be conventional fixed bed reactors (tube bundle reactors, adiabatic fixed bed reactors, circulation reactors). An MTBE-containing reaction mixture is drawn off from the last of the fixed bed reactors in each case. The distillative removal of the MTBE-containing fraction from the reaction mixture can be effected in a single column in the simplest case. This column may also be designed as a reactive distillation in order to further deplete isobutene still present in the reaction mixture. The bottom product obtained is technical MTBE, which can serve as the feedstock (I) for the MTBE cracking. The distillate consists principally of unconverted C4 hydrocarbons which, due to azeotrope formation with methanol, also comprise methanol. The bottom product comprises, as well as MTBE, as a result of the preparation, also other components, for example 2-methoxybutane, C4, C5 and C8 hydrocarbons and water, which are either formed as a by-product in the MTBE synthesis or are already present in the feedstock and are not being removed. Depending on the methanol/isobutene ratio selected and the conversion achieved, methanol may also be present. In the process according to the invention, the MTBE synthesis and the distillation are preferably operated in such a way that the methanol content is at a minimum.

The starting streams for the MTBE synthesis generally comprise, however, not only the C4 hydrocarbons but also oxygen compounds. The type and amount of the oxygen compounds depend on the type and origin of the raw material streams used and the technical conditions selected in the crackers. The further workup of the C4 cut also influences the content of these impurities. The oxygen compounds are especially acetone. Acetone is not removed from the MTBE in the MTBE synthesis and in the subsequent distillation and, as a result of the preparation, at least some gets into the MTBE product. As can be inferred from table 3, technical MTBE, according to the preparation process and raw material stream used, may comprise up to 500 ppm of acetone. It is an object of the invention to remove the acetone very substantially and effectively from the MTBE.

PROCESS STEP B

Low Boiler and Acetone Removal

As already stated above, in the processes known from the literature, the MTBE-containing feedstock (I) is at least optionally freed of low boilers by distillation. The low boilers are predominantly C4 or C5 hydrocarbons. The distillation column is operated in such a way that the low boilers are removed as the top product, and the bottom product comprises the low boilers only up to those limiting concentrations which do not endanger the corresponding specification in the isobutene product (see table 1). In this mode of operation, acetone is not removed. It has been found that, by altering the mode of operation or design of the installation, acetone can in principle also be removed partly via the top by distinctly increasing the amount of distillate and optionally also the reflux ratio. But such a removal by simple distillation of the acetone together with other lower-boiling components as the top product is associated with a disproportionately high energy expenditure and excessively high MTBE and methanol losses, and is therefore not preferred.

According to the invention, the acetone removal is effected in a distillation column K1 in which the MTBE-containing mixture (I) is separated into a top product (II) comprising predominantly the C4 and C5 hydrocarbons, a side stream (III) comprising acetone, methanol and MTBE, and a bottom stream (IV) comprising MTBE.

This substance separation is preferably performed in a distillation column with a side draw which has 20 to 80 theoretical plates, preferably 25 to 60 and more preferably 35 to 55 theoretical plates. The feed stream is applied below the side draw, preferably at least 5 plates below, more preferably at least 10 plates below. The side stream is drawn off preferably between plates 5 and 25, counted from the top, more preferably between plates 10 and 20. Preferably, the column, depending on the number of plates implemented, the composition of the MTBE used and the required purity of the bottom and top products and of the side stream, is operated with a reflux ratio between 100 and 800, especially between 150 and 750. The reflux ratio is defined here as the mass flow of the reflux divided by the mass flow of the distillate. The ratio of mass flow of the side draw (III) to the mass flow of the feed (I) to the column is preferably 0.01 to 0.2, more preferably 0.05 to 0.01. The side stream (III) is preferably drawn off in liquid form. The column is preferably operated at an operating pressure of 0.2 to 0.6 MPa(abs), preferably of 0.3 to 0.4 MPa(abs). The column can be heated using steam, for example. The condensation can, according to the operating pressure selected, be effected against cooling brine, cooling water or air. The top vapours of the column can be condensed completely or only partially, and so the top product (II) can be drawn off either in liquid or vaporous form. The top product (II) can be utilized thermally or used as a feedstock for other processes, for example in a synthesis gas plant.

Preferably, by adjusting the distillation conditions, greater than 50% by mass of the acetone supplied is removed through the side stream (II), more preferably greater than 75% by mass. The bottom product (IV) comprises preferably less than 50% by mass of the acetone supplied, more preferably less than 80% by mass. The concentration of acetone in the bottom product (IV) is preferably less than 50 ppm, more preferably less than 30 ppm.

It should be pointed out that the acetone removal can also be effected in a dividing wall column. Dividing wall columns are distillation columns which have a longitudinal division in some regions. The longitudinal division, which is in the form of a wall welded in a fixed manner or loosely inserted, prevents cross-mixing of liquid and vapour streams in the sub-region of the column in question. In the case of a design of the column K1 as a dividing wall column, the side stream (III) is drawn off in the region of the dividing wall. This has the advantage of greater enrichment of acetone in the side draw (III), and that the side draw (III) comprises a lower level of C4 and C5 hydrocarbons.

PROCESS STEP C

High Boiler Removal

In a preferred embodiment, after the first distillation to remove acetone and low boilers in process step b), in a process step c), the MTBE stream (IV) is purified further in a further distillation. In this step, high boilers, in particular C8 hydrocarbons, such as diisobutene, are removed as the bottom product. A further task of this column may be the partial or complete removal of 2-methoxybutane, since 2-methoxybutane can be cracked in the MTBE cracking reactor to give linear butenes and methanol. Linear butenes in excessively high concentration can in some cases endanger the isobutene specification.

The distillative separation of the MTBE stream (IV) which has been freed of acetone and low boilers into an MTBE-comprising top stream (VI) and a bottom stream (V) comprising higher-boiling compounds than MTBE in process step c) is effected preferably in at least one column, preferably in exactly one distillation column K2.

If, more particularly, only C8 hydrocarbons are to be removed in column K2, it may be advantageous when the column has 15 to 60 theoretical plates, preferably 20 to 55 and more preferably 30 to 45 theoretical plates. The reflux ratio, defined in the context of the present invention as the mass flow of the reflux divided by the mass flow of the distillate, is, depending on the number of plates implemented, the composition of the MTBE used and the purity required, preferably adjusted to a value of 0.5 to 7, preferably of 1 to 4.

If C8 hydrocarbons and additionally 2-methoxybutane are to be removed in column K2, the distillation column used has preferably from 50 to 140 theoretical plates, more preferably from 60 to 120 and most preferably from 80 to 110. The reflux ratio is, depending on the number of plates implemented, the composition of the MTBE used and the purity required, preferably from 1 to 20, more preferably from 2.5 to 10. Even if the removal of 2-methoxybutane should be unnecessary, the design of the column with a higher number of plates need not be a disadvantage since some of the higher capital investment for the larger column can be compensated for by saving energy (reduction of the reflux ratio). At the same time, this gives higher operative flexibility.

The operating pressure of column K2 may preferably be from 0.1 to 2.0 MPa(abs). When the MTBE fraction (VI) obtained at the top of the column is cracked in the MTBE cracking reactor in process step d), in the gas phase at elevated pressure, it may be advantageous to perform the distillation at higher pressure, in which case the top condenser is preferably operated as a partial condenser and the top product (VI) is drawn off in vaporous form. The top product drawn off in vaporous form can then be supplied to the reactor directly or after further preheating. The pressure difference between distillation and reactor here is preferably at least 0.05 $MPa_{(abs)}$. If the reaction pressure in the cracking reactor is, for example, 0.7 $MPa_{(abs)}$, the distillation pressure should preferably be at least 0.75 $MPa_{(abs)}$. At operating pressures of greater than 0.95 $MPa_{(abs)}$, it is possible to use the heat of condensation to raise (low-pressure) steam, with which other columns in the process can be heated. The column can be heated, according to the operating pressure selected, using steam or heat carrier oil.

The top product (VI) of column K2 comprises preferably less than 2500 ppm of 2-methoxybutane, more preferably less than 2000 ppm. Stream (VI), due to its purity, can be used as a solvent and extractant in the pharmaceutical sector and in analysis. This stream, however, preferably serves as a feed stream to MTBE cracking for preparation of high-purity isobutene.

The bottom product (V) of column K2 comprises the C8 hydrocarbon and 2-methoxybutane high boilers, and MTBE. If principally C8 hydrocarbons, for example diisobutene, are to be removed in the column, the MTBE content in the bottom product can be reduced to values less than 25% by mass. If 2-methoxybutane is to be removed in addition, due to the small boiling point differences between 2-methoxybutane and MTBE, a higher MTBE content in the bottom product between 60 and 85% by mass will appropriately be permitted in order to reduce the complexity of the separation. In both cases, this mixture can be utilized thermally, used as a feedstock for a synthesis gas plant or used as a fuel component directly or after hydrogenation.

PROCESS STEP D

MTBE Cracking

In step d) of the process according to the invention, the MTBE stream (IV) obtained in process step b), optionally after preceding removal of higher-boiling components in process step c) as stream (VI), is cracked in one or more reactors to give isobutene and methanol. The MTBE cracking is preferably effected in the gas phase over a heterogeneous catalyst. In this step, it is possible to use all solid catalysts which bring about the cracking of MTBE to isobutene and methanol within the temperature range of 150 to 500° C., especially within the range from 200 to 400° C.

The catalysts used in the process according to the invention may, for example, contain metal oxides, mixed metal oxides, especially those which contain silicon oxide and/or aluminium oxide, acids on metal oxide supports or metal salts or mixtures thereof.

In the process according to the invention, MTBE is cracked to isobutene and methanol in the gas phase preferably using catalysts which consist in a formal sense of magnesium oxide, aluminium oxide and silicon oxide. Such catalysts are described, for example, in U.S. Pat. No. 5,171,920 in example 4 or in EP 0 589 557.

Particular preference is given to using catalysts which, in a formal sense, comprise magnesium oxide, aluminium oxide and silicon dioxide, and which have a proportion of magnesium oxide of 0.5 to 20% by mass, preferably of 5 to 15% by mass and more preferably of 10 to 15% by mass, a proportion of aluminium oxide of 4 to 30% by mass, preferably of 10 to 20% by mass, and a proportion of silicon dioxide of 60 to 95% by mass, preferably of 70 to 90% by mass. It may be advantageous when the catalyst comprises an alkali metal oxide in addition to the magnesium oxide. This may, for example, be selected from $Na_2O$ or $K_2O$. The catalyst preferably comprises $Na_2O$ as the alkali metal oxide. The catalyst used with preference preferably has a BET surface area (determined volumetrically with nitrogen to DIN ISO 9277) of 200 to 450 $m^2/g$, preferably of 200 to 350 $m^2/g$. When the catalyst is applied as an active material on a support, only the active material has a BET surface area within the range specified. The material composed of catalyst and support may, in contrast, according to the properties of the support, have a significantly different BET surface area, especially a lower BET surface area.

The pore volume of the catalyst is preferably 0.5 to 1.3 ml/g, preferably 0.65 to 1.1 ml/g.

The mean pore diameter to DIN 66133 of the catalyst is preferably 5 to 20 nm, preferentially 8 to 15 nm. More preferably, at least 50% by mass, preferably more than 70% by mass, of the total pore volume (sum of the pore volume of the pores with a pore diameter of greater than or equal to 3.5 nm, determined by mercury porosimetry to DIN 66133) of the catalyst, is accounted for by pores having a diameter of 3.5 to 50 nm (mesopores).

In the process according to the invention, preference is given to using catalysts which have a mean particle size (determined by screen analysis) of 10 μm to 10 mm, preferably 0.5 mm to 10 mm, more preferably a mean particle size of 1 to 5 mm. Preference is given to using solid catalysts which have a mean particle size $d_{50}$ of 2 to 4 mm, especially of 3 to 4 mm.

In the process according to the invention, the catalyst can be used in the form of shaped bodies. The shaped bodies may assume any shape. Preference is given to using the catalyst as shaped bodies in the form of spheres, extrudates or tablets. The shaped bodies preferably have the abovementioned mean particle sizes.

The preparation and use of such magnesium aluminosilicate catalysts is described in DE 10 2006 040432. Reference is made thereto.

The MTBE is cracked in the gas phase within the temperature range from 150 to 500° C., especially 200 to 400° C., at pressures of 0.05 to 2 MPa, especially at pressures of 0.3 to 1 MPa, very particularly at pressures of 0.5 to 0.7 MPa.

The cracking of MTBE to isobutene and methanol is an endothermic reaction. In order to prevent partial condensation of MTBE and products, it is appropriate to operate the reactor such that the minimum temperature in the reactor is greater than 150° C., preferably greater than 200° C. The inlet temperature of the MTBE, which can be established by means of a heater connected upstream of the reactor, is therefore at least 150° C., preferably at least 200° C.

In the course of operation, it may be advantageous to raise the inlet temperature and/or operating temperature up to 500°

C. with increasing deactivation of the catalyst to keep the conversion constant. When the conversion can no longer be maintained on attaining of 500° C., it may be advantageous to completely or partially replace the catalyst.

The conversion of the MTBE in step d) of the process according to the invention is between 40% and 99%, preferably between 70% and 98%, more preferably between 85% and 95%.

The reactor is preferably operated with a weight hourly space velocity (WHSV, in kilograms of reactant per kilogram of catalyst per hour) of 0.1 to 5 $h^{-1}$, especially of 1 to 3 $h^{-1}$, in straight pass.

The reactors used are preferably tubular reactors or tube bundle reactors, especially those with internal tube diameters of 10 to 60 mm. They are preferably operated as described in DE 10 2006 040433.

Side reactions occur in the cracking of MTBE. These are attributable either to MTBE or the isobutene and methanol cracking products. Standard reactions which occur in MTBE cracking are the formation of dimethyl ether (DME) from methanol and the formation of $C_8$ hydrocarbons by dimerization of isobutene. Reaction of isobutene with water can additionally result in formation of tert-butanol (TBA); conversely, TBA present in the reactor feed can be cracked to give water and isobutene.

In addition to the side reactions, there are usually also parallel reactions in which impurities from the MTBE react. These include, for example, the cracking of 2-methoxybutane present in the MTBE. Through elimination of methanol, these can form 1-butene and 2-butenes. 3-methoxy-1-butene or 1-methoxy-2-butene present in the MTBE can form 1,3-butadiene in the cracking.

PROCESS STEP E

Purification of the Cracking Products

In order to work up the cracking product mixture further, it may be advantageous when the cracking product (VII) is separated in a further distillation in process step d) into an isobutene-comprising top stream (IX) and an unconverted MTBE-comprising bottom stream VIII. The distillative separation of the cracking product (VII) into an isobutene-comprising top stream (IX) and an unconverted MTBE-comprising bottom stream (VIII) in process step d) is preferably effected in at least one column, preferably in exactly one distillation column K3.

A distillation column K3 used with preference in process step e) has preferably from 20 to 55 theoretical plates, more preferably from 25 to 50 and especially preferably from 30 to 45 theoretical plates. The reflux ratio is, depending on the number of plates implemented, the composition of the reactor output and the purities of distillate and bottom product required, preferably less than 5, more preferably less than 1. The operating pressure of column K3 can preferably be set between 0.1 and 2.0 MPa(abs). In order to dispense with a compressor, it may be advantageous to operate the column at a lower pressure than the pressure with which the cracking reactor R in process step b) is operated. In order to be able to condense isobutene against cooling water, a pressure of approx. 0.5 MPa(abs) is needed. If the cracking in process step b) is conducted, for example, at a pressure of 0.65 MPa (abs), it may be advantageous when the distillation column of process step c) is operated with an operating pressure of 0.55 to 0.6 MPa (abs). The vaporizer can be heated using, for example, 0.4 MPa steam. The bottom product (VIII) comprises preferably unconverted MTBE, methanol and any by-products, for example diisobutene and 2-methoxybutane. The top product is preferably isobutene with a purity greater than 95% by mass, based on the overall top product.

The bottom product (VIII) obtained in process step e) comprises the MTBE unconverted in process step d), and the majority of the methanol formed in the cracking of the MTBE. The bottom product may comprise by-products, for example diisobutene and/or 2-methoxybutane. There are various options for the use or workup of this stream (VIII). If the MTBE cracking plant is in an integrated system with a plant for preparation of MTBE, stream (VIII) can be conducted into the MTBE plant, preferably into the synthesis section. This is true even when the MTBE plant produces only just as much MTBE as is required for the cracking and thus no further outlet for high-boiling components is present in the synthesis section. A second option is to distillatively remove the majority of the methanol from the stream VIII and to return the rest to process step b). The latter option is especially advantageous for standalone plants in which delivered MTBE is used.

Acetone is partly removed into the bottom product (VIII) in distillation column K3; only small fractions of the acetone present in the feed stream (VII) get into the distillate (IX). If, however, as described above, the bottom stream (VIII) is returned upstream of the reaction section R, acetone accumulates to undesirably high concentrations without the inventive removal in process step b). Preferably between 90 and 99% by mass of the acetone present in the reactor output (VII) is removed via the bottom product (VIII). In the absence of discharge of acetone in process step b), this means, however, that acetone will accumulate in the circuit to such high concentrations that virtually the entire amount of the acetone present in stream (I) gets into the top product (IX) of column K3. This is prevented by the inventive discharge in process step b).

The top product (IX), which is obtained in process step d), in accordance with the invention is virtually free of acetone and consists preferably to an extent of greater than 95% by mass of isobutene can be used directly as a saleable product or purified further.

Since isobutene forms a minimum azeotrope with methanol, the top product (IX) obtained in process step e), in addition to the main isobutene product, may comprise especially methanol. As further components, the top product (IX) may comprise, for example, dimethyl ether which may have formed, for example, as a result of condensation of methanol, and linear butenes (1-butene, cis-2-butene, trans-2-butene) which may have formed, for example, as a result of decomposition of 2-methoxybutane, and water.

PROCESS STEP F

Isobutene Workup

Isobutene qualities available on the market are typically virtually free of methanol; see table 1. The methanol can be removed from the stream (IX) obtained in process step e) by processes known per se, for example by extraction. The extraction of methanol from stream (IX) can be performed, for example, with water or an aqueous solution as an extractant, for example in an extraction column. The extraction with water or an aqueous solution is preferably performed in an extraction column K4, which preferably has from 4 to 16 theoretical plates. The extractant (XIII) can flow through the extraction column in cocurrent or countercurrent in relation to the stream to be extracted. The extractant (XIII) is preferably conducted through the extraction column in countercurrent in relation to the stream to be extracted. The extraction is performed preferably at a temperature of 15 to 50° C., more preferably 25 to 40° C. For example, in the case of use of an extraction column having more than six theoretical plates, which is operated at a pressure of 0.9 MPa(abs) and a temperature of 40° C., a water-saturated isobutene with an isobutene content of more than 99% by mass can be obtained.

The methanol-containing water extract (XI) obtained in the extraction can be separated by distillation into water and methanol. The separation is preferably effected in a distillation column K5. The water can be recycled into the extraction stage as extractant (XIII). The methanol (XII) can be used for customary technical syntheses, for example esterifications or etherifications. The methanol is preferably recycled into the MTBE synthesis from which the starting stream (I) originates.

Any acetone present in the isobutene-containing stream (IX) is not removed to a noticeable degree in the extraction due to the solution equilibria and remains partly in the moist isobutene stream (X).

The moist isobutene stream (X) from the extraction column can be separated from dimethyl ether and water in a further distillation column K6 and worked up to give dry isobutene. The dry isobutene is obtained as the bottom product (XVI). In the condensation system at the top of the column, after phase separation, water (XIV) is drawn off in liquid form and dimethyl ether (XV) in gaseous form. A distillation column used with preference for the drying has preferably from 30 to 80 theoretical plates, more preferably from 40 to 70 theoretical plates. The reflux ratio is, depending on the number of plates implemented and the required purity of the isobutene, preferably less than 100, more preferably less than 75. The operating pressure of column K2 can preferably be set between 0.1 and 2.0 MPa(abs).

Any acetone present in stream (X) is not removed to a noticeable degree in distillation column K6 due to the boiling point situation (see table 2) and in this case remains partly in the isobutene product (XVI).

According to the invention, however, acetone is discharged in the acetone removal in process step b), such that stream (X) in accordance with the invention is free of acetone. The isobutene obtained in this way may have, for example, the composition detailed in table 1. According to the purity requirements, however, lower concentrations of the secondary components are also conceivable if required.

A block diagram of a preferred embodiment with which the process according to the invention can be performed is shown in FIG. 1. The starting MTBE (I) is supplied to column K1. In column K1, the MTBE-containing mixture (I) is separated into a top product (II) which comprises predominantly the C4 and C5 hydrocarbons, a side stream (III) which comprises acetone, methanol and MTBE, and a bottom stream (IV) which comprises MTBE. The bottom stream (IV) comprises preferably less than 50% by mass of the acetone present in the starting stream (I).

Figure 2:
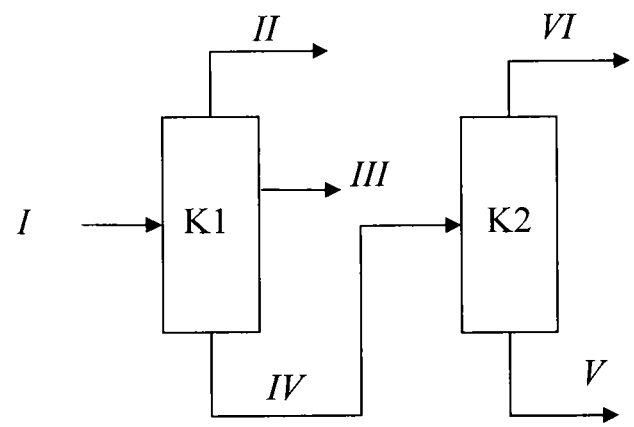
FIG. 2 is a block diagram of a second preferred embodiment of a process for purifying technical MTBE according the invention.

A further preferred embodiment of the process is shown in FIG. 2. In this case, the removal in stream (I) of the acetone present, of the methanol and of the low boilers present, especially C4 and C5 hydrocarbons, is effected analogously to FIG. 1 in column K1. The bottom stream (IV) of column K1 is passed into column K2. High boilers present (C8 hydrocarbons, for example diisobutene, 2-methoxybutane) are at least partly removed therein as bottom product (V). The top product (VI) is MTBE which has been substantially freed of low boilers, methanol, acetone and high boilers and can, due to its purity, be used as a solvent and extractant in the pharmaceutical sector and in analysis. More particularly, the bottom product (VI) is also suitable as a feedstock for the preparation of high-purity isobutene by back-cracking of MTBE to isobutene and methanol.

Figure 3:
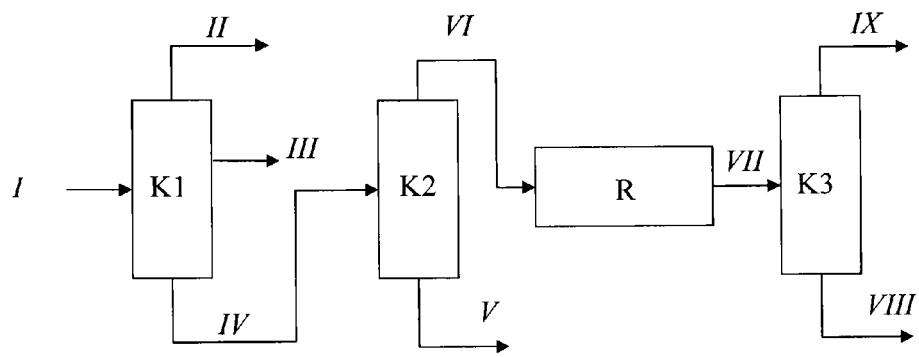
FIG. 3 is the block diagram of FIG. 2 further depicting an MTBE back-cracking column K-3 for separating isobutene.

Such a process for preparing isobutene by back-cracking MTBE is shown in FIG. 3. The process according to FIG. 3 is a further preferred embodiment of the process. The starting MTBE (I) is worked up analogously to FIG. 2 in columns K1 and K2. The top product (VI) of column K2 is conducted into the cracking reactor R. The cracking product (VII) is separated in column K3 into a top product (IX) comprising the isobutene formed, DME and, due to azeotrope formation between isobutene and methanol, fractions of methanol, and into a bottom product (VIII) comprising the unconverted MTBE and the majority of the methanol formed. According to the invention, acetone is removed partly via the bottom in column K3. According to the invention, stream (VII) comprises only such a low level of acetone that the acetone which gets into the top product does not endanger the isobutene specification. The bottom product (VIII) can optionally, after removal of methanol, be recycled upstream of column K1, be recycled into an MTBE synthesis S1 or be used in some other way.

Figure 4:
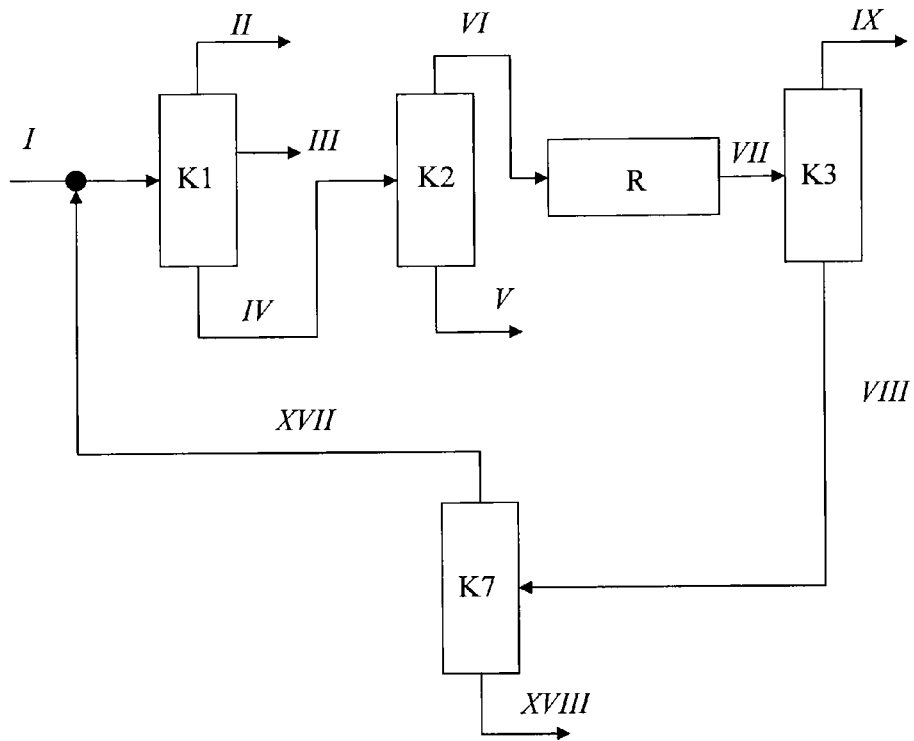
FIG. 4 is the block diagram of FIG. 3 further depicting a first preferred embodiment for recycling the bottom stream VIII of column K-3.
Figure 5:
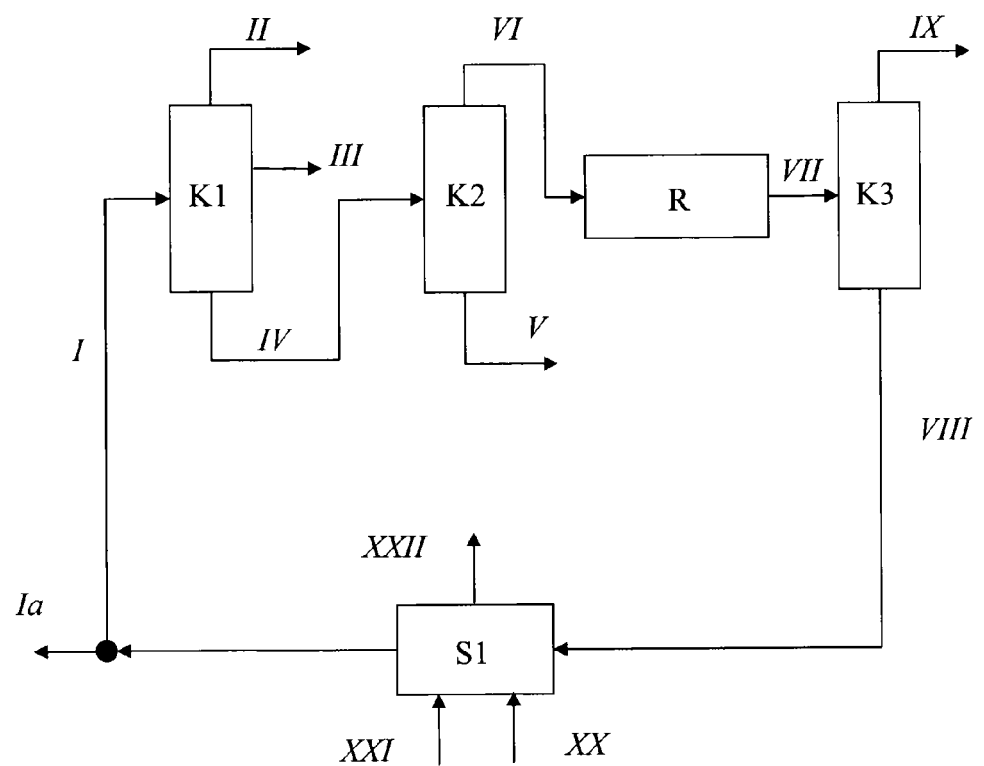
FIG. 5 is the block diagram of FIG. 3 further depicting a second preferred embodiment for recycling the bottom stream VIII of column K-3.

Preferred embodiments for recycling of the bottom stream (VIII) of column K3 are shown in FIGS. 4 and 5.

FIG. 4 shows a preferred embodiment of the process, in which the bottom stream (VIII) of column K3, after removal of methanol, is recycled upstream of column K1. The majority of the methanol is removed as bottom product (XVIII) from stream (VIII) in column K7. The top product (XVII), which comprises MTBE and portions of methanol, is fed to column K1. In column K7, the predominant portion of the acetone present in stream (VIII) remains in the top product and is discharged in accordance with the invention in the side draw (III) in column K1.

FIG. 5 comprises a preferred embodiment of the process, in which the bottom stream (VIII) of column K3 is recycled into an MTBE synthesis S1. Supplied to the MTBE synthesis S1 are at least one isobutene-containing C4 hydrocarbon stream (XX) and a methanol-containing stream (XXI). Stream (XXI) may, for example, comprise fresh methanol or methanol which has been recovered in the extraction of methanol-containing C4 streams with water and subsequent methanol/water separation within the process. The methanol present in stream (XXI) is reacted with the isobutene present in (XX) to give MTBE in the MTBE synthesis S1. This MTBE is used, directly or after distillative removal of a stream (XXII), as MTBE-containing stream (I) in step a) of the process according to the invention. If a stream (XXII) is removed before use in step a), it comprises at least the majority of the unconverted C4 hydrocarbons and also fractions of methanol. This embodiment may be advantageous especially when the distillative removal of stream (XXII) is executed in the form of a reactive distillation column. The use of reactive distillation columns in MTBE synthesis is prior art and is used to increase the conversion of isobutene to MTBE.

The MTBE-containing stream (I) is supplied to column K1 as described. Optionally, a stream (Ia) can be discharged and marketed, for example, as technical MTBE. In this preferred embodiment, some acetone present in stream (XX) gets into stream (I) and is discharged from the process via stream (III). The concentration of acetone in the circuit (streams (IV), (VI), (VII) and (VIII)) is so low that acetone does not get into the isobutene product (IX) to a significant degree.

According to the water content of streams (XX) and (XXI), in the process variant according to FIG. 5, water has to be discharged from the process. Preferred variants for water discharge are described in DE 10 2009 027404.

Figure 6:
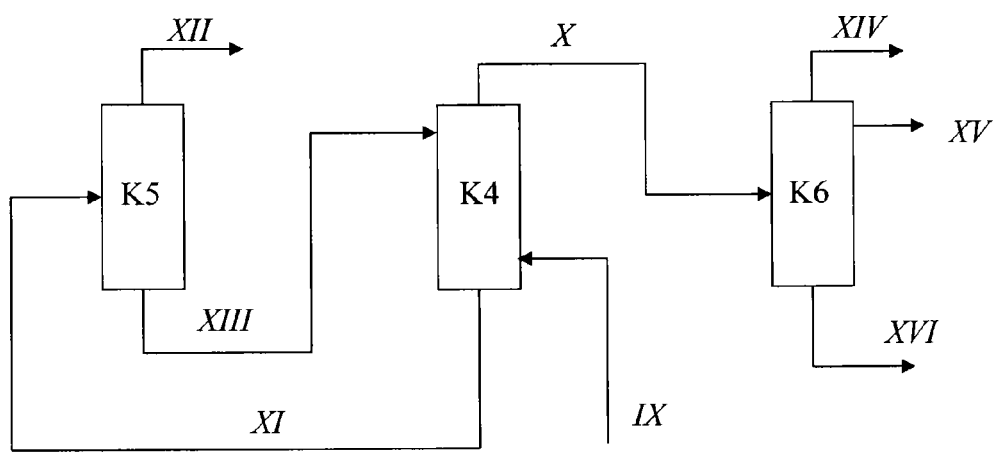
FIG. 6 is the block diagram of FIG. 3 further depicting a preferred embodiment for the further workup of the isobutene stream IX of column K-3.

FIG. 6 shows a preferred embodiment for the further workup of the methanol-containing isobutene stream (IX) obtained in process step e). Methanol is washed out of stream (IX) with water (XIII) in an extraction column K4. The methanol-laden water (XI) is separated in column K5 into a methanol-containing stream (XII) and water (XIII); the water is recycled into the extraction. Stream (XII) is preferably returned to an MTBE synthesis, more preferably to the MTBE synthesis from which stream (I) originates. The water-saturated isobutene stream (X) which still comprises DME is then purified further in column K6. At the top of the column, a DME-containing stream (XIV) is obtained, which normally also comprises isobutene. To remove the water, it is advisable to equip the column K6 with a top decanter in which the water (XV) separates out as a second phase and can be discharged. In the bottom of the column, isobutene (XV) is obtained. Any acetone present in stream (IX) is not fully removed either in column K4 or in column K6 and therefore most of it gets into the isobutene product (XVI). According to the invention, stream (IX), however, is very substantially free of acetone, and so stream (XVI) is also very substantially free of acetone.

When columns are used in the process according to the invention, for example the columns designated K1 to K7 in FIGS. 1 to 6, they can be provided with internals, which, for example, are composed of trays, rotating internals, random packings and/or structured packings.

In the case of column trays, for example, the following types can be used:
- trays with bores or slots in the tray plate.
- trays with necks or chimneys which are covered by caps or hoods.
- trays with bores in the tray plate, which are covered by movable valves.
- trays with special constructions.

In the case of use of columns with random packings comprising various packing materials, the packing materials may consist of almost all materials, especially of steel, stainless steel, copper, carbon, stoneware, porcelain, glass or plastics, and have a wide variety of different shapes, especially the shape of spheres, rings with smooth or profiled surfaces, rings with internal struts or wall breaches, wire mesh rings, saddles and spirals.

Structured packings with regular/ordered geometry may consist, for example, of sheet metal or fabric. Examples of such packings are Sulzer BX fabric packings made of metal or plastic, Sulzer Mellapak lamellar packings made of sheet metal, high-performance packings from Sulzer such as Mella-pakPlus, and structured packings from Sulzer (Optiflow), Montz (BSH) and Kühni (Rombopak).

The isobutene prepared by the process according to the invention can, for example, be used to prepare methacrylic acid, methyl methacrylate, diisobutene, polyisobutene, alkylphenols, methallyl chloride or methallyl sulphonates. In particular, it may be advantageous to use both the methanol obtained in the cracking and the isobutene to prepare methyl methacrylate. Such a process of preparing methyl methacrylate is described, for example, in EP 1 254 887, to which explicit reference is made.

The examples which follow are intended to illustrate the invention.

EXAMPLES

Example 1

The MTBE cracking was carried out in a tubular reactor with a heating jacket, through which a heat carrier oil (Marlotherm SH from Sasol Olefins & Surfactants GmbH) flowed. The catalyst used was magnesium-doped silica-alumina. The catalyst was prepared according to patent application DE 10 2006 040432; see example 2. The reactant used was high-purity MTBE, which is normally not used as a fuel additive but as a solvent (DRIVERON-S from Evonik Oxeno GmbH).

Before entry into the reactor, the MTBE was vaporized completely in an evaporator at 260° C. The cracking was carried out at a temperature of 261° C. (temperature of the Marlotherm in the feed of the reactor jacket); the pressure was set to a constant 0.7 $MPa_{(abs)}$ by a pressure-maintaining means at the end of the reactor. The MTBE feed was regulated to a constant 1500 g/h, which corresponds to a WHSV of 4.53 $h^{-1}$ at an amount of catalyst of 331 g. The gaseous cracking mixture leaving the reactor was condensed fully and analysed by gas chromatography.

After an operating time of 1600 hours, the conversion of the MTBE under the reaction conditions selected was 90.6%, the selectivity for dimethyl ether was 3.53% and the selectivity for diisobutene was 0.05%. After 1613 hours, acetone was metered into the reactor feed; the reactor feed and the reactor output were analysed for acetone by means of GC analysis. The results are shown in table 4.

TABLE 4

Analyses of reactor feed and reactor output (in each case parts by mass)

| Time [h] | Acetone conc. in the feed [ppm by mass] | Acetone conc. in the output [ppm by mass] |
|---|---|---|
| 1613 | 342 | 320 |
| 1627 | 320 | 315 |
| 1681 | 300 | 298 |
| 1705 | 311 | 310 |
| 1729 | 258 | 253 |
| 1753 | 299 | 280 |
| 1797 | 314 | 320 |
| 1837 | 314 | 325 |
| 1849 | 310 | 305 |

No noticeable decrease in acetone was detected; the recovery rate in all cases is above 90% by mass and hence within the range of measurement accuracy. During the metered addition of acetone, methyl vinyl ketone (up to 8 ppm) and 2-methoxypropene (up to 2 ppm) were detected in traces.

The conversion of MTBE and selectivities for dimethyl ether and diisobutene remained unchanged.

This example showed that acetone is not noticeably degraded in the reaction section of the MTBE cracking and hence, when present in the reactor feed, is also present in virtually unchanged concentration in the output of the reaction section.

Explanations for Examples 2, 3, 4 and 5

In examples 2, 3, 4 and 5 which follow, calculations were conducted with the steady-state simulation program ASPEN Plus (2006 version from AspenTech), which further illustrate the invention and show the effects of the acetone discharge on the overall process of MTBE cracking.

In order to obtain transparent reproducible data, only substance data which is generally available was used. In the examples, the "NRTL-RK" property method (see H. Renon and J. M. Prausnitz, "Local Compositions in Thermodynamic Excess Functions for Liquid Mixtures," AIChE J., Vol. 14, No. 1, (1968), pp. 135-144 and O. Redlich and J. N. S. Kwong, "On the Thermodynamics of Solutions V. An Equation-of-state. Fugacities of Gaseous Solutions," Chem. Rev., Vol. 44, (1979), pp. 223-244) was used.

For the modelling of reactors RS1-1, RS1-2 and RS1-3 in the MTBE synthesis and of the cracking reactor R in the MTBE cracking, kinetic reactor models based on extensive experimental test data with the respective catalysts were used in the calculations. The examples therefore each also specify the reaction temperatures which were assumed in the reactor modelling. Since the composition of the incoming and outgoing streams of the reaction stages is also specified in each case, it is possible for the person skilled in the art, by reworking the reactors with fixed conversions, to rework the example without knowing the exact equations for the kinetics.

Example 2a

Noninventive

In example 2a, a column K1* is considered, in which MTBE-containing starting stream (I) is merely freed of low boilers such as C4 and C5 hydrocarbons. Such a column is described in most of the processes known from the literature, for example DE 10 2009 027404. Accordingly, in column K1* the MTBE-containing feedstock (I) is separated into a top product (II*) and a bottom product (IV*). As a feed to column K1*, an MTBE stream (I) (MTBE-containing starting stream) of 1000 kg/h with the composition listed in table 5 is assumed (typical fuel MTBE, compare with table 3).

TABLE 5

Composition of the assumed MTBE entry stream (I) and of the distillate (II*) and of the bottom product (IV*) for column K1* for example 2a

|  | Starting MTBE (I) | K1* distillate (I*) | K1* bottom prod. (IV*) |
|---|---|---|---|
| Mass flow rate [kg/h] | 1000.0 | 4.2 | 995.8 |
| Parts by mass [kg/kg] |  |  |  |
| dimethyl ether |  |  |  |
| isobutene |  |  |  |
| n-butane | 0.000150 | 0.035549 |  |
| 1-/2-butenes | 0.001030 | 0.244102 |  |
| C5 hydrocarbons | 0.002000 | 0.462191 | 0.000050 |
| MTBE | 0.979165 | 0.150000 | 0.982679 |
| 2-methoxybutane | 0.002500 | 0.000064 | 0.002510 |
| methanol | 0.009500 | 0.108011 | 0.009083 |
| tert-butanol | 0.003000 |  | 0.003013 |
| water | 0.000005 | 0.000005 | 0.000005 |
| diisobutene | 0.002500 |  | 0.002511 |
| acetone | 0.000150 | 0.000078 | 0.000150 |

Column K1* has 40 theoretical plates and is operated at a pressure of 0.35 $MPa_{(abs)}$. Feed (I) is applied above plate 15, counted from the top. The reflux was set to 671 kg/h, such that the MTBE content in the distillate (II*) is firstly low (MTBE loss), and the bottom product (IV*) is secondly very substantially free of low boilers (C4 and C5 hydrocarbons). The distillate of this column K1* has a residual content of 15% by mass of MTBE and the bottom product a residual content of C4 and C5 hydrocarbons of 50 ppm. The acetone present in the starting MTBE (150 ppm) is not removed in this operating mode of the column; the concentration in the bottom product (IV*) is unchanged at 150 ppm.

This example showed that, in a customary operating mode of the low boiler column described in the literature, acetone is not removed from the starting MTBE (I).

Example 2b

Noninventive

In example 2b, the distillate mass flow rate of column K1* is adjusted such that, with the same reflux flow rate, 80% by mass of the acetone present in feed stream (I) is separated into the distillate. Mass flow rate and composition of feed stream (I), and pressure, number of plates and application level for column K1* remain unchanged from example 2a.

The mass flow rates and the corresponding composition of distillate (II*) and bottom product (IV*) are shown in table 6.

TABLE 6

Composition of the distillate (II*) and of the bottom product (IV*) for column K1* for example 2b

|  | K1* distillate (I*) | K1* bottom prod. (IV*) |
|---|---|---|
| Mass flow rate [kg/h] | 232.9 | 767.1 |
| Parts by mass [kg/kg] |  |  |
| dimethyl ether |  |  |
| isobutene |  |  |
| n-butane | 0.000644 |  |
| 1-/2-butenes | 0.004423 |  |
| C5 hydrocarbons | 0.008570 | 0.000006 |
| MTBE | 0.942549 | 0.990281 |
| 2-methoxybutane | 0.001066 | 0.002935 |
| methanol | 0.040794 |  |
| tert-butanol | 0.001417 | 0.003480 |
| water | 0.000021 |  |
| diisobutene |  | 0.003259 |
| acetone | 0.000515 | 0.000039 |

As is evident from table 6, the distillate mass flow rate has to be increased from 4.2 kg/h in Example 2a to 233 kg/h in order to remove 80% by mass of the acetone present in feed stream (I) from the bottom product (IV*). The MTBE content in the distillate is approx. 94% by mass. Thus, the MTBE loss is considerable (22% by mass). The content of C4 and C5 hydrocarbons in the distillate totals approx. 1.4% by mass. Thus, this stream is unsuitable as a fuel additive without being worked up again.

Example 2c

Noninventive

In example 2c, the reflux flow rate of column K1* is increased to 947 kg/h and the distillate mass flow rate of column K1* is adjusted such that 80% by mass of the acetone present in feed stream (I) is again separated into the distillate. Mass flow rate and composition of feed stream (I) and pressure, number of plates and application level for column K1* remain unchanged from example 2a.

The mass flow rates and the corresponding composition of distillate (II*) and bottom product (IV*) are shown in table 7.

TABLE 7

Composition of the distillate (II*) and of the bottom product (IV*) for column K1* for example 2c

|  | K1* distillate (I*) | K1* bottom prod. (IV*) |
|---|---|---|
| Mass flow rate [kg/h] | 130.2 | 869.8 |
| Parts by mass [kg/kg] |  |  |
| dimethyl ether |  |  |
| isobutene |  |  |
| n-butane | 0.001152 |  |
| 1-/2-butenes | 0.007909 |  |
| C5 hydrocarbons | 0.015331 | 0.000004 |
| MTBE | 0.900536 | 0.990939 |
| 2-methoxybutane | 0.000530 | 0.002795 |

TABLE 7-continued

Composition of the distillate (II*) and of the bottom product (IV*) for column K1* for example 2c

|  | K1* distillate (I*) | K1* bottom prod. (IV*) |
|---|---|---|
| methanol | 0.072946 | |
| tert-butanol | 0.000638 | 0.003354 |
| water | 0.000038 | |
| diisobutene | | 0.002874 |
| acetone | 0.000921 | 0.000034 |

In spite of an increase in the reflux, approx. 11% by mass of the MTBE present in the feed stream is still discharged via the distillate (MTBE loss). The content of C4 and C5 hydrocarbons in distillate (I*) has increased to approx. 2.4% by mass compared to example 2b. Thus, this stream is unsuitable as a fuel additive without being worked up again.

Example 3a

Inventive

Example 3a corresponds to the process shown in FIG. 1. Column K1, in contrast to column K1* in examples 2a and 2b, is operated with a side draw (III). Mass flow rate and composition of feed stream (I) remain unchanged from example 2a.

Column K1 has 52 theoretical plates and is operated at a pressure of 0.35 MPa$_{(abs)}$. Feed (I) is applied above plate 27, counted from the top. Side draw (II) is withdrawn in liquid form from plate 12 and is adjusted to 70 kg/h. The reflux rate was selected as in example 2a (670 kg/h).

TABLE 8

Composition of distillate (II), of side draw (III) and of bottom product (IV) for column K1 for example 3a

|  | K1 distillate (I) | K1 bottom prod. (IV) | K1 side draw (III) |
|---|---|---|---|
| Mass flow rate [kg/h] | 4.0 | 926.0 | 70.0 |
| Parts by mass [kg/kg] | | | |
| dimethyl ether | | | |
| isobutene | | | |
| n-butane | 0.036276 | | 0.000054 |
| 1-/2-butenes | 0.245209 | | 0.000593 |
| C5 hydrocarbons | 0.460260 | 0.000023 | 0.001758 |
| MTBE | 0.150000 | 0.991320 | 0.866124 |
| 2-methoxybutane | 0.000018 | 0.002670 | 0.000391 |
| methanol | 0.107805 | | 0.129506 |
| tert-butanol | | 0.003222 | 0.000235 |
| water | 0.000009 | | 0.000071 |
| diisobutene | | 0.002700 | |
| acetone | 0.000424 | 0.000064 | 0.001267 |

The distillate (II) of this column K1 has, as in example 2a, a residual content of 15% by mass of MTBE, while the bottom product (IV) comprises only 23 ppm of C5 hydrocarbons (see table 8). The acetone present in the starting MTBE (150 ppm) in this operating mode is discharged via the side stream (II) to an extent of approx. 60% by mass; the bottom stream (IV) comprises only approx. 40% by mass of the original amount. As can be inferred from table 8, the distillate mass flow rate (I) remains virtually unchanged from example 2a, and hence also the MTBE loss via this stream. In the side stream, only approx. 6% by mass of the amount of MTBE present in the feed stream is discharged. In contrast to the distillate streams in examples 2b and 2c, the content of C4 and C5 hydrocarbons in the side stream, however, is low (approx. 2400 ppm), and so this stream (II) can be marketed as a fuel additive, optionally also after mixing with a stream from an MTBE synthesis.

Example 3b

Inventive

In example 3b, the reflux flow rate of column K1, as in example 2c, is increased to 947 kg/h and the distillate mass flow rate of column K1* is adjusted such that the distillate (II) again comprises a residual content of 15% by mass of MTBE. Composition of the feed stream (I) and pressure, number of plates and application level for feed stream and withdrawal level for the side draw for column K1 remain unchanged from example 3a.

The mass flow rates and the corresponding composition of distillate (II), side draw (III) and bottom product (IV) are shown in table 9.

TABLE 9

Composition of distillate (II), of side draw (III) and of bottom product (IV) for column K1 for example 3b

|  | K1 distillate (I) | K1 bottom prod. (IV) | K1 side draw (III) |
|---|---|---|---|
| Mass flow rate [kg/h] | 4.1 | 925.9 | 70.0 |
| Parts by mass [kg/kg] | | | |
| dimethyl ether | | | |
| isobutene | | | |
| n-butane | 0.035756 | | 0.000038 |
| 1-/2-butenes | 0.242768 | | 0.000426 |
| C5 hydrocarbons | 0.462660 | 0.000004 | 0.001295 |
| MTBE | 0.150000 | 0.991366 | 0.866584 |
| 2-methoxybutane | 0.000015 | 0.002676 | 0.000323 |
| methanol | 0.108231 | | 0.129344 |
| tert-butanol | | 0.003222 | 0.000237 |
| water | 0.000009 | | 0.000071 |
| diisobutene | | 0.002700 | |
| acetone | 0.000562 | 0.000032 | 0.001681 |

The increase in the reflux makes it possible to remove 80% by mass of the acetone present in the feed stream via the side draw and distillate, the side draw comprising approx. 79% by mass of the acetone. In contrast to examples 2b and 2c, however, the MTBE loss via the distillate (I) is low, and again only approx. 6% by mass of the amount of MTBE present in the feed stream is discharged via the side draw. Compared to example 3a, increasing the reflux allowed the content of C4 and C5 hydrocarbons in the side stream to be reduced further (approx. 1760 ppm), such that this stream (II) can again be marketed as a fuel additive.

Examples 2a, 2b, 2c, 3a and 3b showed that, in a customary operating mode of the low boiler column K1* described in the literature, acetone is not removed from the starting MTBE (I). By increasing the distillate mass flow rate (II)* and the reflux, it is possible with the same configuration (column K1* without side draw) to remove acetone, but an undesirably high MTBE loss is associated with this operating mode. With the inventive configuration of the low boiler column—column K1 with side draw—acetone can be removed effectively and with lower MTBE losses.

Example 4

Inventive

Example 4 corresponds to the process described in FIG. 5 for preparation of high-purity isobutene, assuming a variant according to FIG. 6 for the purification of the isobutene (IX).

As the feed to the MTBE synthesis S1, according to FIG. 5, a C4 hydrocarbon stream (XX) of 1800 kg/h with the composition listed in table 10 with a proportion of 60 ppm of acetone is assumed (typical raffinate I). Also listed in table 10 is likewise the composition and the mass flow rate of the fresh methanol supplied (XX). Composition and mass flow rate of the recycled stream (VIII) coming from process step e) (column K3 bottom product) are shown in table 13. The amount of fresh methanol was adjusted so as to result in a molar ratio of methanol to isobutene in the feed to the MTBE synthesis of 1.13.

TABLE 10

Composition of the entry stream (XX) and of the fresh methanol (XXI), and of the distillate (XII) and of the bottom product (I) (starting MTBE) of column KS1-1 for example 4

|  | Raffinate I (XX) | Methanol (XXI) | KS1-1 distillate (XXII) | Starting MTBE (I) |
|---|---|---|---|---|
| Mass flow rate [kg/h] | 1800.0 | 120.1 | 1249.5 | 1117.1 |
| Parts by mass [kg/kg] | | | | |
| dimethyl ether | | | 0.000709 | |
| isobutane | 0.025500 | | 0.036736 | |
| isobutene | 0.350000 | | 0.020956 | |
| n-butane | 0.080000 | | 0.115250 | |
| butadiene | 0.001500 | | 0.002161 | |
| 1-/2-butenes | 0.542400 | | 0.779989 | 0.000441 |
| C5 hydrocarbons | 0.000540 | | 0.000056 | 0.000808 |
| MTBE | | | | 0.972864 |
| 2-methoxybutane | | | | 0.003335 |
| methanol | | 1.000000 | 0.043415 | 0.009500 |
| tert-butanol | | | | 0.011162 |
| water | | | 0.000727 | 0.000003 |
| diisobutene | | | | 0.001768 |
| acetone | 0.000060 | | | 0.000119 |

The C4 hydrocarbon stream (XX), the fresh methanol (XXI) and the methanol-containing recycle stream (VIII) are mixed in process step S1 and supplied to an MTBE synthesis. The MTBE synthesis consists, in Example 4, of three series-connected adiabatic fixed bed reactors RS1-1, RS1-2 and RS1-3 and a distillation column KS1-1. The first reactor RS1-1 is designed as a circulation reactor. Filling of the reactors with Amberlyst® 15 (Rohm & Haas) is assumed. Reactor RS1-1 is modelled with a capacity of 3.25 m$^3$, RS1-2 with 1.8 W and RS1-3 with 1 m$^3$. The inlet temperature into reactor RS1-1 is 42° C., the circulation flow rate assumed 5100 kg/h. The inlet temperature into reactor RS1-2 is 40° C., the inlet temperature into reactor RS1-3 36° C. Under these conditions, a conversion of isobutene over all three reactors of approx. 96% is found. Side reactions considered in the kinetic model used are the formation of TBA from isobutene and water, the dimerization of isobutene to diisobutene, the reaction of methanol to give DME and water, and the formation of 2-methoxybutane from n-butenes.

The reactor output from reactor RS1-3 is supplied to column KS1-1. The column has 70 theoretical plates and the feed is above plate 50, counted from the top. The column is operated at a reflux ratio of 0.9 and at a pressure of 0.65 MPa$_{(abs)}$. The bottom product (I) (starting MTBE) is technical MTBE; see table 10. In column KS1-1, acetone passes completely into the bottoms. The distillate (XXII) consists predominantly of C4 hydrocarbons and of methanol, DME formed in the MTBE synthesis and water. In further workup steps known from the literature, for example extraction, the distillate (XXII) can be freed of oxygenates and processed further to give further products of value.

The MTBE stream (I) comprises a total of approx. 1250 ppm of C4 and C5 hydrocarbons, and approx. 120 ppm of acetone. According to the invention, the C4 and C5 hydrocarbons and the acetone are removed from this stream in column K1. Column K1 has, as in examples 3a and 3b, 52 theoretical plates and is operated at a reflux rate of 1341 kg/h and at a pressure of 0.35 MPa$_{(abs)}$. Feed (I) is applied above plate 27, counted from the top. The side draw (II) is withdrawn in liquid form from plate 12 and set to 70 kg/h.

Table 11 shows the composition of distillate (II), of side draw (III) and of bottom product (IV) of column K1.

TABLE 11

Composition of distillate (II), of side draw (III) and of bottom product (IV) of column K1 for example 4

|  | K1 distillate (I) | K1 side draw (III) | K1 bottom prod. (IV) |
|---|---|---|---|
| Mass flow rate [kg/h] | 1.8 | 70.0 | 1045.2 |
| Parts by mass [kg/kg] | | | |
| dimethyl ether | | | |
| isobutane | | | |
| isobutene | | | |
| n-butane | 0.000004 | | |
| butadiene | | | |
| 1-/2-butenes | 0.264378 | 0.000133 | |
| C5 hydrocarbons | 0.476646 | 0.000424 | 0.00001 |
| MTBE | 0.150000 | 0.848364 | 0.982642 |
| 2-methoxybutane | 0.000017 | 0.000369 | 0.003539 |
| methanol | 0.108444 | 0.148768 | |
| tert-butanol | | 0.000384 | 0.011903 |
| water | 0.000005 | 0.000051 | |
| diisobutene | | | 0.001889 |
| acetone | 0.000506 | 0.001507 | 0.000025 |

The distillate of column K1 has a residual content of 15% by mass of MTBE. The side stream comprises the predominant portion of the acetone present in stream (I) (approx. 79% by mass), while the bottom product (IV), in accordance with the invention, comprises only a very low level of acetone (25 ppm, 20% by mass of the amount present in stream (I)).

The MTBE stream (IV) which has been freed of low boilers and acetone is supplied to column K2 in which principally diisobutene and 2-methoxybutane are removed via the bottom (V). The column has 105 theoretical plates and is operated at a reflux ratio of 3.2 and at a pressure of 0.8 MPa(abs). Stream (IV) is added above plate 40, counted from the top. The top product (VI) obtained is a gaseous fraction comprising more than 98% by mass of MTBE. The 2-methoxybutane content in the distillate was adjusted to 2000 ppm by mass (see table 12). In this column, the acetone passes completely into the distillate.

TABLE 12

Composition of bottom product (V) and of distillate (VI) of column K2, and of reactor output (VII) from reactor R, for example 4

|  | K2 bottom prod. (V) | K2 distillate (VI) | Reactor output (VII) |
|---|---|---|---|
| Mass flow rate [kg/h] | 20.9 | 1024.3 | 1024.3 |
| Parts by mass [kg/kg] | | | |
| dimethyl ether | | | 0.002300 |
| isobutane | | | |

TABLE 12-continued

Composition of bottom product (V) and of distillate (VI) of
column K2, and of reactor output (VII) from reactor R,
for example 4

|  | K2 bottom prod. (V) | K2 distillate (VI) | Reactor output (VII) |
|---|---|---|---|
| isobutene |  |  | 0.539935 |
| n-butane |  |  |  |
| butadiene |  |  |  |
| 1-/2-butenes |  |  | 0.000205 |
| C5 hydrocarbons |  | 0.000001 | 0.000001 |
| MTBE | 0.826570 | 0.985827 | 0.147638 |
| 2-methoxybutane | 0.078959 | 0.002000 | 0.001678 |
| methanol |  |  | 0.301598 |
| tert-butanol |  | 0.012146 | 0.003024 |
| water |  |  | 0.003116 |
| diisobutene | 0.094471 |  | 0.000480 |
| acetone |  | 0.000026 | 0.000026 |

After further heating to reaction temperature, the MTBE fraction (VI) is supplied, according to FIG. 5, to the cracking reactor in process step d). The cracking reactor is modelled with a reactor capacity of 0.9 m$^3$, assuming filling with a catalyst which consists formally of magnesium oxide, aluminium oxide and silicon oxide, the preparation of which is described in patent DE 102006040432.7.

The reactor is run at 289° C. and 0.7 MPa$_{(abs)}$. Under these reaction conditions, an MTBE conversion of approx. 85% is found; the conversion of 2-methoxybutane is approx. 16%. Due to the restriction in the proportion of 2-methoxybutane to 2000 ppm by mass in the reactor feed, however, in spite of the cracking of 2-methoxybutane to 1- and 2-butene, there is no risk to a specification customary on the market for linear butenes in the isobutene product. For acetone, in accordance with example 1, no conversion is assumed. The composition of the reactor output (IV) is shown in table 12.

The reactor output (VII) is partly condensed and fed in biphasic form to column K3. The column has 45 theoretical plates and is operated at a reflux ratio of 0.3 and at a pressure of 0.65 MPa(abs). The feed stream (VI) is added above plate 28, counted from the top. The bottom product consists predominantly of unconverted MTBE (approx. 33% by mass) and methanol (approx. 64% by mass), and also the predominant portion of the acetone present in the feed stream (56 ppm); see table 13. Stream (VIII) is recycled into the MTBE synthesis S1.

The top product (IX) is isobutene with a purity of greater than 95% by mass of isobutene. The limits for linear butenes (<1000 ppm by mass) and C5 hydrocarbons (<1000 ppm by mass) required in a typical isobutene specification are complied with in a reliable manner; see also table 1. Acetone is present only in a concentration of 3 ppm, which, however, still corresponds to approx. 6% by mass of the amount of acetone present in the feed stream (VII).

TABLE 13

Composition of bottom product (VIII) and of distillate (IX) of
column K3 for example 4

|  | K3 bottom prod. (VIII) | K2 distillate (IX) |
|---|---|---|
| Mass flow rate [kg/h] | 446.4 | 577.9 |
| Parts by mass [kg/kg] |  |  |
| dimethyl ether | 0.000019 | 0.004061 |
| isobutane |  |  |
| isobutene | 0.000500 | 0.956601 |
| n-butane |  |  |
| butadiene |  |  |
| 1-/2-butenes | 0.000025 | 0.000344 |
| C5 hydrocarbons | 0.000001 |  |
| MTBE | 0.338774 | 0.000001 |
| 2-methoxybutane | 0.003850 |  |
| methanol | 0.642355 | 0.038392 |
| tert-butanol | 0.006940 |  |
| water | 0.006377 | 0.000598 |
| diisobutene | 0.001102 |  |
| acetone | 0.000056 | 0.000003 |

In the extraction K4, stream (IX) is washed with water (XI) in order to remove the methanol still present. Column K4 has 5 theoretical plates and is operated at a pressure of 1.2 MPa$_{(abs)}$. The fresh water (XIII) is applied at plate 1, counted from the top; the methanol-laden water (XI) (aqueous phase) is drawn off at plate 5 and the moist, methanol-free isobutene stream (X) (organic phase) is drawn off at plate 1.

TABLE 14

Composition of the fresh water, of the organic phase (X) and
of the aqueous phase (XI) of column K4 for example 4

|  | Fresh water (XIII) | K4 organic phase (X) | K4 aqueous phase (XI) |
|---|---|---|---|
| Mass flow rate [kg/h] | 100.0 | 555.5 | 122.4 |
| Parts by mass [kg/kg] |  |  |  |
| dimethyl ether |  | 0.003929 | 0.001342 |
| isobutane |  |  |  |
| isobutene |  | 0.994815 | 0.001612 |
| n-butane |  |  |  |
| butadiene |  |  |  |
| 1-/2-butenes |  | 0.000358 | 0.000001 |
| C5 hydrocarbons |  |  |  |
| MTBE |  | 0.000001 |  |
| 2-methoxybutane |  |  |  |
| methanol |  | 0.000002 | 0.181264 |
| tert-butanol |  |  |  |
| water | 1.000000 | 0.000892 | 0.815776 |
| diisobutene |  |  |  |
| acetone |  | 0.000002 | 0.000005 |

The compositions of the fresh water, of the organic phase (X) and of the aqueous phase (XI) of column K4 are shown in table 14.

Optionally, stream (XI) can be separated again into water and methanol in a further distillation column K5, as shown in FIG. 6.

The moist isobutene stream (X) is virtually methanol-free, but still comprises DME. The acetone was depleted slightly in the extraction.

The isobutene stream (X) is supplied to column K6, in order to remove residual water and dimethyl ether. The column has 70 theoretical plates and is operated at a reflux ratio of 81 and at a pressure of 1.0 MPa$_{(abs)}$. The feed stream (X) is added above plate 8, counted from the top. The column has a top decanter on which water (XV) is drawn off as the second phase.

The compositions of the distillate (XIV), of the aqueous phase (XV) of the top decanter and of the bottom product (XVI) of column K6 are shown in table 15.

TABLE 15

Composition of the distillate (XIV), of the aqueous phase (XV) of the top decanter, and of the bottom product (XVI) of column K6 for example 4

| | K6 distillate (XIV) | K6 decanter aq. phase (XV) | K6 bottom prod. (XVI) |
|---|---|---|---|
| Mass flow rate [kg/h] | 18.2 | 0.3 | 537.0 |
| Parts by mass [kg/kg] | | | |
| dimethyl ether | 0.119747 | 0.014149 | |
| isobutane | | | |
| isobutene | 0.870535 | 0.000425 | 0.999629 |
| n-butane | | | |
| butadiene | | | |
| 1-/2-butenes | 0.000067 | | 0.000368 |
| C5 hydrocarbons | | | |
| MTBE | | | 0.000001 |
| 2-methoxybutane | | | |
| methanol | 0.000061 | 0.000665 | |
| tert-butanol | | | |
| water | 0.009590 | 0.984760 | |
| diisobutene | | | |
| acetone | | | 0.000002 |

The distillate (XIV) of column K6 still comprises approx. 87% by mass of isobutene. DME can optionally be concentrated to a higher level in a further column, and the isobutene can be recycled into column K6.

The bottom product is isobutene with a purity greater than 99.9% by mass and meets the specification according to table 1. More particularly, the oxygenates total less than 10 ppm; the acetone concentration is 2 ppm.

Example 5

Noninventive

Example 4 serves as a comparative example and does not include the process according to the invention. Accordingly, a process similar to FIG. 5 is considered, except that process step b), i.e. the discharge of the acetone in the side draw of column K1, is omitted. The place of column K1 with a side draw is taken by a simple distillation column K1* according to example 2a. All other process steps and column configurations remain unchanged from example 5.

The feed to the MTBE synthesis S1 is assumed, analogously to example 4, to be a C4 hydrocarbon stream (XX) of 1800 kg/h with unchanged composition; see table 10. Table 16 lists the composition and the mass flow rate of the fresh methanol (XX) supplied. The composition and mass flow rate of the recycle stream (VIII) coming from process step e) (column K3 bottom product) are shown in table 19. The amount of fresh methanol was adjusted so as again to result in a molar ratio of methanol to isobutene in the feed to the MTBE synthesis of 1.13.

TABLE 16

Composition of the fresh methanol (XXI) and of the distillate (XII) and of the bottom product (I) (starting MTBE) of column KS1-1 for example 5

| | KS1-1 distillate (XXII) | Methanol (XXI) | Starting MTBE (I) |
|---|---|---|---|
| Mass flow rate [kg/h] | 1800.0 | 90.8 | 1129.3 |
| Parts by mass [kg/kg] | | | |
| dimethyl ether | | | |
| isobutane | 0.025500 | | |
| isobutene | 0.350000 | | |
| n-butane | 0.080000 | | |
| butadiene | 0.001500 | | |
| 1-/2-butenes | 0.542400 | | 0.000453 |
| C5 hydrocarbons | 0.000540 | | 0.000824 |
| MTBE | | | 0.969930 |
| 2-methoxybutane | | | 0.003418 |
| methanol | | 1.000000 | 0.009500 |
| tert-butanol | | | 0.012502 |
| water | | | 0.000004 |
| diisobutene | | | 0.001776 |
| acetone | 0.000060 | | 0.001594 |

The C4 hydrocarbon stream (XX), the fresh methanol (XXI) and the methanol-containing recycle stream (VIII) are mixed in process step S1 and supplied to an MTBE synthesis. The arrangement of the reactors, reactor sizes and inlet temperatures remain unchanged from example 4. Under these conditions, an overall conversion of isobutene of approx. 96% is again found. The reactor output from reactor RS1-3 is again supplied to column KS1-1. The number of plates, reflux ratio and column pressure remain unchanged from example 4. The composition and mass flow rate of distillate (XXII) and bottom product (I) (starting MTBE) are shown in table 16. It should be noted that, due to the lack of removal in column K1 and the associated increased acetone concentration in the reflux stream (VIII), the acetone concentration in the starting MTBE (I) has risen distinctly to approx. 1600 ppm compared to example 4.

In column K1* the C4 and C5 hydrocarbons are removed from the MTBE stream (I). Column K1* has, as in example 2a, 40 theoretical plates and is operated at a pressure of 0.35 MPa$_{(abs)}$. The feed (I) is applied above plate 15, counted from the top. In order to achieve, analogously to example 2a, a concentration of 50 ppm of C4 and C5 hydrocarbons in the bottom product (IV*), the column is operated at a reflux rate of 826 kg/h. Table 17 shows the composition of the distillate stream (II*) and of the bottom stream (IV*) of column K1*.

TABLE 17

Composition of the distillate (II*) and of the bottom product (IV*) for column K1* for example 5

| | K1* distillate (I*) | K1* bottom prod. (IV*) |
|---|---|---|
| Mass flow rate [kg/h] | 1.9 | 1127.4 |
| Parts by mass [kg/kg] | | |
| dimethyl ether | | |
| isobutane | | |
| isobutene | | |
| n-butane | 0.000004 | |
| butadiene | | |
| 1-/2-butenes | 0.273941 | |
| C5 hydrocarbons | 0.467714 | 0.000050 |
| MTBE | 0.150000 | 0.971288 |
| 2-methoxybutane | 0.000086 | 0.003424 |
| methanol | 0.107314 | 0.009338 |
| tert-butanol | | 0.012523 |
| water | 0.000006 | 0.000004 |
| diisobutene | | 0.001778 |

TABLE 17-continued

Composition of the distillate (II*) and of the bottom product (IV*) for column K1* for example 5

|  | K1* distillate (I*) | K1* bottom prod. (IV*) |
|---|---|---|
| acetone | 0.000936 | 0.001595 |

Acetone in this operating mode, as already shown in example 2a, is not removed and discharged from the process.

The MTBE stream (IV*) is supplied to column K2, in which diisobutene and 2-methoxybutane are removed via the bottom (V). The number of plates and column pressure remain unchanged from example 4. The reflux ratio is 2.9. Compositions and mass flow rates of top and bottom product of column K2 are shown in table 18. The acetone in this column again passes completely into the distillate.

TABLE 18

Composition of the bottom product (V) and of the distillate (VI) of column K2 and of the reactor output (VII) from the reactor R for example 5

|  | K2 bottom prod. (V) | K2 distillate (VI) | Reactor output (VII) |
|---|---|---|---|
| Mass flow rate [kg/h] | 22.5 | 1104.9 | 1104.9 |
| Parts by mass [kg/kg] |  |  |  |
| dimethyl ether |  |  | 0.002344 |
| isobutane |  |  |  |
| isobutene |  |  | 0.533905 |
| n-butane |  |  |  |
| butadiene |  |  |  |
| 1-/2-butenes |  |  | 0.000205 |
| C5 hydrocarbons |  | 0.000051 | 0.000051 |
| MTBE | 0.837882 | 0.974011 | 0.145868 |
| 2-methoxybutane | 0.073196 | 0.002000 | 0.001678 |
| methanol |  | 0.009529 | 0.307412 |
| tert-butanol |  | 0.012778 | 0.003182 |
| water |  | 0.000004 | 0.003253 |
| diisobutene | 0.088922 |  | 0.000474 |
| acetone |  | 0.001628 | 0.001628 |

The MTBE fraction (VI) is, after vaporization and further heating to reactor temperature, supplied according to FIG. 5 to the cracking reactor in process step d). The reactor volume, catalyst charge and reaction pressure remain unchanged from example 4. The reactor temperature is raised to 292° C. in order again to achieve an MTBE conversion of approx. 85% and a 2-methoxybutane conversion of approx. 16%. For acetone, again no conversion is assumed. The composition of the reactor output (IV) is shown in table 18.

The reactor output (VII) is partially condensed and supplied in biphasic form to column K3. The number of plates, reflux ratio and column pressure remain unchanged from example 4. As in example 4, again only approx. 6% by mass of the acetone present in the feed stream (VII) is distilled into the top product (IX); approx. 94% by mass of the acetone passes into the bottom product (VIII); see table 19. Since, however, the concentration in the feed is very high due to lack of an acetone discharge, approx. 170 ppm of acetone gets into the top product.

TABLE 19

Composition of the bottom product (VIII) and of the distillate (IX) of column K3 for example 5

|  | K3 bottom prod. (XIII) | K2 distillate (IX) |
|---|---|---|
| Mass flow rate [kg/h] | 488.4 | 616.5 |
| Parts by mass [kg/kg] |  |  |
| dimethyl ether | 0.000021 | 0.004184 |
| isobutane |  |  |
| isobutene | 0.000500 | 0.956450 |
| n-butane |  |  |
| butadiene |  |  |
| 1-/2-butenes | 0.000025 | 0.000348 |
| C5 hydrocarbons | 0.000082 | 0.000026 |
| MTBE | 0.330005 | 0.000001 |
| 2-methoxybutane | 0.003796 |  |
| methanol | 0.647238 | 0.038214 |
| tert-butanol | 0.007198 |  |
| water | 0.006596 | 0.000604 |
| diisobutene | 0.001073 |  |
| acetone | 0.003466 | 0.000172 |

Stream (VIII) is recycled into the MTBE synthesis S1; the top product (IX) is worked up further in columns K4 and K6 analogously to example 4. The number of plates and column pressure remain unchanged for both columns from example 4. Column K6 is operated at a reflux ratio of 73. The corresponding compositions of the streams are shown in tables 20 and 21.

TABLE 20

Composition of the fresh water, of the organic phase (X) and of the aqueous phase (XI) of column K4 for example 5

|  | Fresh water (XIII) | K4 organic phase (X) | K4 aqueous phase (XI) |
|---|---|---|---|
| Mass flow rate [kg/h] | 100.0 | 592.7 | 123.8 |
| Parts by mass [kg/kg] |  |  |  |
| dimethyl ether |  | 0.004060 | 0.001401 |
| isobutane |  |  |  |
| isobutene |  | 0.994541 | 0.001717 |
| n-butane |  |  |  |
| butadiene |  |  |  |
| 1-/2-butenes |  | 0.000361 | 0.000001 |
| C5 hydrocarbons |  | 0.000027 |  |
| MTBE |  | 0.000001 |  |
| 2-methoxybutane |  |  |  |
| methanol |  | 0.000003 | 0.190243 |
| tert-butanol |  |  |  |
| water | 1.000000 | 0.000894 | 0.806316 |
| diisobutene |  |  |  |
| acetone |  | 0.000112 | 0.000323 |

TABLE 21

Composition of the distillate (XIV), of the aqueous phase (XV) of the top decanter and of the bottom product (XVI) of column K6 for example 5

|  | K6 distillate (XIV) | K6 decanter aq. phase (XV) | K6 bottom prod. (XVI) |
|---|---|---|---|
| Mass flow rate [kg/h] | 20.1 | 0.3 | 572.3 |
| Parts by mass [kg/kg] |  |  |  |
| dimethyl ether | 0.119758 | 0.014157 |  |
| isobutane |  |  |  |
| isobutene | 0.870501 | 0.000426 | 0.999483 |

TABLE 21-continued

Composition of the distillate (XIV), of the aqueous phase (XV) of the top decanter and of the bottom product (XVI) of column K6 for example 5

|  | K6 distillate (XIV) | K6 decanter aq. phase (XV) | K6 bottom prod. (XVI) |
|---|---|---|---|
| n-butane |  |  |  |
| butadiene |  |  |  |
| 1-/2-butenes | 0.000069 |  | 0.000372 |
| C5 hydrocarbons |  |  | 0.000028 |
| MTBE |  |  | 0.000001 |
| 2-methoxybutane |  |  |  |
| methanol | 0.000081 | 0.000875 |  |
| tert-butanol |  |  |  |
| water | 0.009589 | 0.984537 |  |
| diisobutene |  |  |  |
| acetone | 0.000003 | 0.000005 | 0.000116 |

As evident from tables 20 and 21, acetone is slightly depleted in the extraction column K4, but the isobutene product (XVI) reaches a value of 116 ppm which clearly exceeds the required specification in table 1 (oxygenates less than 10 ppm).

The comparison of example 4 (inventive) and example 5 (noninventive) displayed the advantages of the process according to the invention in a very graphic manner. As a result of the lack of process step b) (acetone discharge), acetone accumulates in the circuit and gets into the isobutene product is undesirably high concentrations.

LIST OF REFERENCE NUMERALS (I), (Ia) MTBE-containing stream or technical MTBE
(II) Top product comprising C4 and C5 hydrocarbons from K1
(III) Side stream comprising acetone, methanol and MTBE from K1
(IV) Bottom product comprising MTBE from K1
(V) Bottom product of K2 comprising higher-boiling components than MTBE
(VI) MTBE-containing top product of K2
(VII) Cracking product of K2 comprising at least MTBE, isobutene and methanol
(VIII) Bottom product comprising MTBE and methanol from K3
(IX) Top product comprising isobutene from K3
(X) Isobutene-enriched stream from K4
(XI) Methanol-comprising extraction stream from K4
(XII) Top product comprising methanol from K5
(XIII) Bottom product of K5 and/or extractant for K4
(XIV) Top product comprising water from K6
(XV) Side stream comprising dimethyl ether from K6
(XVI) Bottom product comprising isobutene from K6
(XVII) Top product comprising MTBE from K7
(XVIII) Bottom product comprising methanol from K7
(XX) Isobutene-containing stream for S1
(XXI) Methanol-containing stream for S1
(XXII) MTBE-containing product from S1
(K1) Distillation column in process step b)
(K2) Distillation column in process step c)
(K3) Distillation column in process step e)
(K4) Distillation column in process step f)
(K5) Distillation column
(K6) Distillation column
(K7) Distillation column
(R) MTBE cracking in process step d)
(S1) MTBE synthesis

The invention claimed is:

1. A process for purifying technical MTBE, the process comprising distillatively separating a technical MTBE (I) comprising MTBE, methanol, C4 hydrocarbons, C5 hydrocarbons and acetone, into:
   a top product (II) comprising C4 and C5 hydrocarbons,
   a side stream (III) comprising acetone, methanol and MTBE, and
   a bottom product (IV) comprising MTBE.

2. The process according to claim 1, wherein the bottom product (IV) comprises less than 50% by mass of the acetone present in the technical MTBE (I).

3. The process according to claim 1, wherein the separating is performed in a distillation column and the side stream (III) is withdrawn in liquid form.

4. The process according to claim 1, further comprising distillatively separating the bottom product (IV) into a top product (VI) comprising MTBE and a bottom product (V) comprising higher-boiling components than MTBE.

5. The process according to claim 4, wherein the top product (VI) has a concentration of less than 2500 ppm by mass of 2-methoxybutane.

6. The process according to claim 4, wherein the bottom product (IV) or the top product (VI) comprises less than 50 ppm by mass of acetone.

7. The process according to claim 4, further comprising catalytically cracking the top product (VI) to obtain a cracking product (VII) comprising MTBE, isobutene and methanol.

8. The process according to claim 7, wherein the cracking is performed over a solid catalyst in a gas phase within a temperature range from 150 to 500° C.

9. The process according to claim 7, comprising separating the cracking product (VII) in a further distillation into a top product (IX) comprising isobutene and a bottom product (VIII) comprising MTBE and methanol.

10. The process according to claim 9, wherein the top product (IX) comprises less than 10 ppm by mass of acetone.

11. The process according to claim 9, comprising removing methanol by extraction, dimethyl ether by distillation, or both, from the top product (IX).

12. The process according to claim 11, wherein the removing comprises:
   extraction by means of an extractant;
   removing an extraction stream (XI) comprising methanol; and
   removing a stream (X) comprising isobutene.

13. The process according to claim 12, comprising separating the extraction stream (XI) by a distillation into a top product (XII) comprising methanol and a bottom product (XIII) comprising the extractant.

14. The process according to claim 9, wherein the bottom product (VIII) is fully or partly recycled into the distillatively separating of the technical MTBE into a top product (II), a side stream (III), and a bottom product (IV).

15. The process according to claim 14, wherein the bottom stream (VIII) is separated in a distillation into a bottom product (XVIII) comprising methanol and a top product (XVII) comprising MTBE, and
   the top product (XVII) is recycled fully or partly into the distillatively separating of the technical MTBE into a top product (II), a side stream (III), and a bottom product (IV).

16. The process according to claim 14, wherein the bottom stream (VIII), a further stream (XXI) comprising methanol and a stream (XX) comprising isobutene are supplied to an MTBE synthesis (S1); and a product (XXII) comprising MTBE is recycled fully or partly into the distillatively separating of the technical MTBE into a top product (II), a side stream (III), and a bottom product (IV).

17. The process according to claim 2, wherein the separating is performed in a distillation column and the side stream (III) is withdrawn in liquid form.

18. The process according to claim 2, further comprising distillatively separating the bottom product (IV) into a top product (VI) comprising MTBE and a bottom product (V) comprising higher-boiling components than MTBE.

19. The process according to claim 3, further comprising distillatively separating the bottom product (IV) into a top product (VI) comprising MTBE and a bottom product (V) comprising higher-boiling components than MTBE.

20. The process according to claim 5, wherein the bottom product (IV) or the top product (VI) comprises less than 50 ppm by mass of acetone.

\* \* \* \* \*